United States Patent [19]

Rose

[11] Patent Number: 4,659,655

[45] Date of Patent: Apr. 21, 1987

[54] METHOD FOR ISOLATING PRODUCT-PRODUCING CELLS

[75] Inventor: Sam Rose, San Francisco, Calif.

[73] Assignee: Bio-Response, Inc., Hayward, Calif.

[21] Appl. No.: 443,191

[22] Filed: Nov. 23, 1982

Related U.S. Application Data

[63] Continuation-in-part of Ser. No. 325,051, Nov. 25, 1981.

[51] Int. Cl.[4] ............... C12N 11/04; G01N 33/53; G01N 33/556; G01N 33/563
[52] U.S. Cl. ..................... 435/7; 435/177; 435/178; 435/182; 435/803; 436/512; 436/520; 436/521; 436/522; 436/535; 436/536; 436/539; 436/821; 436/824
[58] Field of Search ............ 435/7/68, 177, 178, 435/182, 240, 241, 261, 803, 814, 948; 436/512, 519, 828, 829, 535, 536, 539, 63, 520, 521, 522, 821, 824; 424/11

[56] References Cited

U.S. PATENT DOCUMENTS

| | | | |
|---|---|---|---|
| 3,764,479 | 10/1973 | Bergeron et al. | 435/27 |
| 3,843,777 | 10/1974 | Hainski et al. | 436/515 |
| 3,850,578 | 11/1974 | McConnell | 436/536 |
| 3,873,684 | 3/1975 | Fujita | 424/11 X |
| 4,061,466 | 12/1977 | Sjoholm et al. | 436/535 |
| 4,070,243 | 1/1978 | Teodorescu et al. | 435/29 |
| 4,130,634 | 12/1978 | Molinaro et al. | 435/515 |
| 4,142,939 | 3/1979 | Morse et al. | 435/7 |
| 4,190,708 | 2/1980 | Kuo et al. | 435/240 |
| 4,192,917 | 3/1980 | Zurawski, Jr. | 435/236 |
| 4,193,983 | 3/1980 | Ullman et al. | 435/7 |
| 4,235,866 | 11/1980 | Thoma | 436/535 |
| 4,255,411 | 3/1981 | Lim et al. | 436/829 X |
| 4,280,816 | 7/1981 | Elahi | 436/535 |
| 4,342,826 | 8/1982 | Cole | 435/7 |
| 4,356,260 | 10/1982 | Elwing | 435/7 |
| 4,363,799 | 12/1982 | Kung et al. | 435/7 |
| 4,376,165 | 3/1983 | Hornby et al. | 435/188 |
| 4,403,037 | 9/1983 | Coates | 436/520 X |
| 4,409,331 | 10/1983 | Lim | 435/178 |

FOREIGN PATENT DOCUMENTS

| | | | |
|---|---|---|---|
| 0047760 | 4/1981 | Japan | 435/174 |
| 2046209 | 11/1980 | United Kingdom | 435/182 |

OTHER PUBLICATIONS

Ross, et al. "Increased Toxicity of Diptheria Toxin for Human Lympho. Cells Following Covalent Linkage . . . " European J. of Biochemistry 104 ('80) pp. 381–390.

Oeltmann, et al. "A Hybrid Protein Containing the Toxic Subunit of Ricin and the Cell Specific Subunit of HCG" J. of Biological Chemistry 254(4) '79, pp. 1028–1032.

Kohler et al, "Continuous Cultures of Fused Cells Secreting Antibody of Predefined Specificity", Nature vol. 256 (8-1957) pp. 495–497.

Engvall, "Preparation of Enzyme Labelled Staphulococcal Protein A and Its Use for Detection of Antibodies", Scand. Journal of Immunology 8(Suppl. 7) (1978) pp. 25–31.

*Primary Examiner*—Thomas G. Wiseman
*Assistant Examiner*—Elizabeth Weimar
*Attorney, Agent, or Firm*—St.Onge Steward Johnston & Reens

[57] ABSTRACT

The invention relates to techniques for isolating from a mixed population of cells disired living cells either producing and releasing a particular product or having a characteristic molecule on their surface. The isolation techniques depend upon the localized interaction between the product (or molecule) and other agents added to the system such that distinguishable conditions can be caused to occur (or not occur) only in the immediate vicinity of desired cells which produced and released the product or which contain the molecule on their surface.

4 Claims, 33 Drawing Figures

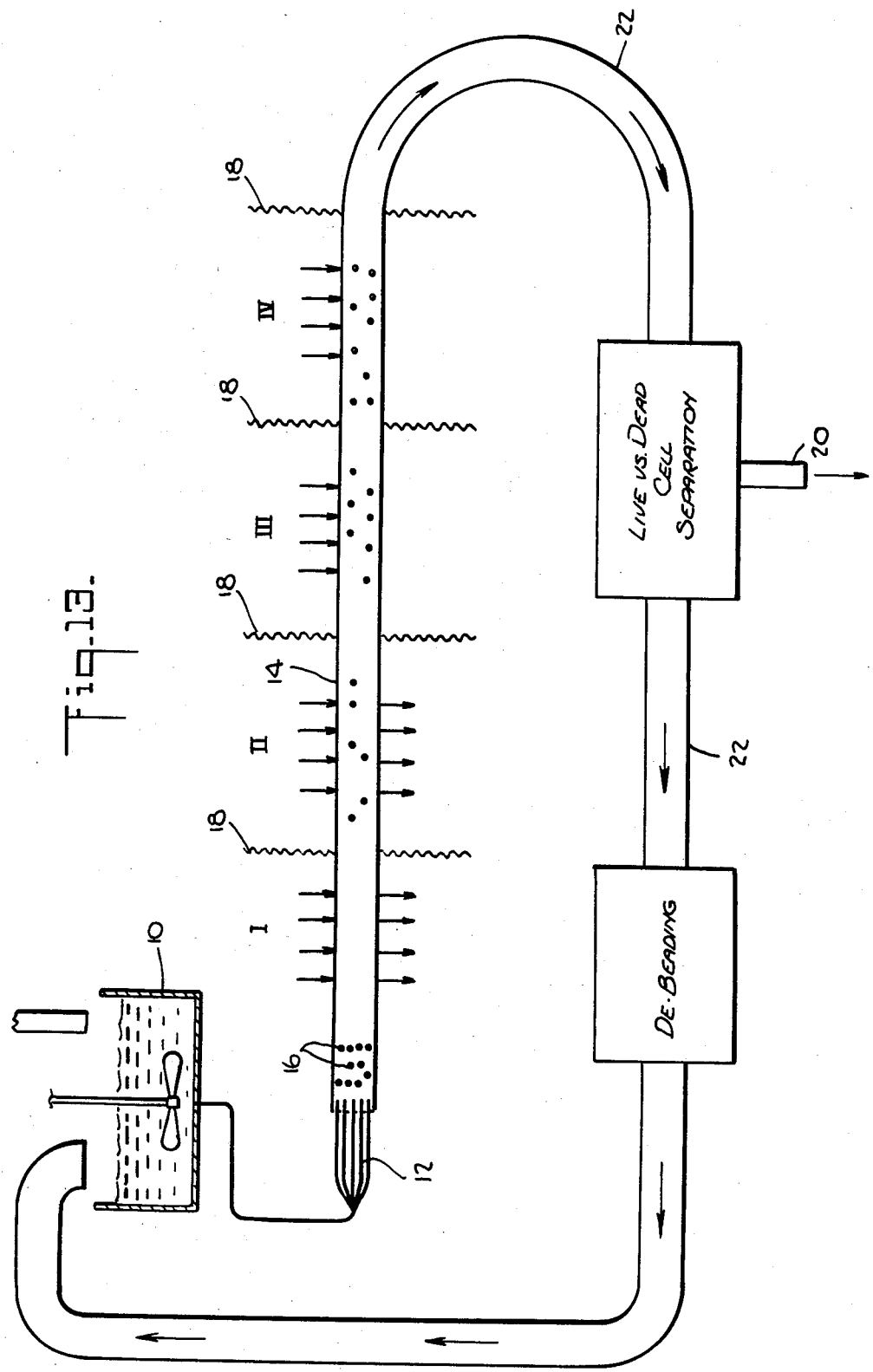

METHOD FOR ISOLATING PRODUCT-PRODUCING CELLS

This application is a continuation-in-part of application Ser. No. 325,051, filed Nov. 25, 1981, now pending.

BACKGROUND OF THE INVENTION

The present invention relates to a method for isolating cells and, more particularly, to a method for isolating "desired" cells from a population of cells, in which population the desired cells are admixed together with "undesired" cells.

In the context of the present invention, the "desired" cells are those living cells producing and releasing a particular product (e.g., antibody) or those living cells producing a particular molecule which, as opposed to being released from the cell, becomes affixed to the cell surface. For each respective case, "undesired" cells simply are those cells not possessing the noted characteristics of the desired cells.

In the various fields of biotechnology such as biochemistry, immunology, biogenetics, and the like, the art worker often is confronted with a cell population containing a large number of cells from which population it is desired to isolate those cells having certain characteristics, particularly the production and release of a desired product or the production of a particular molecule which becomes affixed to the cell surface. Typically, the ratio of these desired cells to the other undesired cells in the population is very small.

By way of illustration, the production of antibodies to a particular antigen typically relies upon the production of antibody by a mammal in response to an administered antigen or in response to a diseased state. Thus, cells removed from an animal or man which has received administered antigen, or which is diseased in such a way as to cause cells in the animal or man to have antigen on their surface, consist of a number of the desired cells, producing antibody, in admixture with many "undesired" cells which are not producing antibody. The isolation from this cell population of the desired, antibody-producing cells is laborious and difficult.

Similar difficulties are encountered in the production of monoclonal antibodies according to recently developed techniques such as hybridization. In hybridization, a collection of cells is harvested from an animal or man which has received administered antigen or which is diseased in a manner which causes cells to have antigen on their surface. The mixed cell collection so obtained contains desired antibody-producing cells in admixture with many cells not producing antibody. The cell population is mixed together with tumor cells such as myeloma cells, in the presence of a fusing agent such as polyethylene glycol, to bring about attachment between myeloma cells and the cells of the mixed cell population, from which attachments hybrid cells can form. Hybrid cells may be isolated from the population in a conventional manner; however, the isolation of desired hybrids, i.e., those hybrids formed between a myeloma cell and an antibody-producing cell and which, in fact, are producing and releasing antibody, is difficult and laborious.

Other situations exist in which the desired cell is one producing and releasing a product other than antibody, for example, an antigen or where the desired cell produces a molecule or product which becomes affixed to the cell surface rather than being released from the cell. In each instance, the isolation of these desired cells from other undesired cells with which they are mixed is difficult.

These difficulties in isolating desired cells from a population containing both these desired cells and undesired cells have spawned a few isolation techniques now practiced in the art. In one method, for isolating cells producing and releasing a desired product, individual cells in the cell population are removed and successively cloned so as to obtain a population of these cells of a size suitable for testing. The fluid in which the clone population is growing may then be tested for the presence of the desired product, a positive response indicating that the cells of the clone population are those making and releasing the desired product. As is apparent, however, this so-called "manual" method is inordinately time-consuming, particularly for typical cell populations containing many millions of cells.

In another method (the "Plaque assay"), suitable for use where the desired cell is one making and releasing an antibody, the population of desired and undesired cells is placed in a gel together with red blood cells having on their surface the appropriate antigen for the antibody released from the desired cells. The antibody released from the desired cells diffuses through the gel and attaches to the antigen on the surface of the red blood cells. The antigen-antibody complex now on the surface of the red blood cell makes it possible to lyse the red blood cell by addition of complement to the entire cell population. The lysed areas in the population can be seen (generally through microscopic examination) as clear areas, and the desired antibody-producing cells will be found in the vicinity (generally, the center) of the clear areas. Apart from being limited to the isolation of only one type of desired cells, this method also suffers from distinct limitations with respect to the number of cells which may be microscopically viewed at any given time and the difficulty of physically removing the desired cells from the indicated areas of the living cell population.

In yet another method, employed for isolating cells by virtue of a characteristic molecule produced by the cell and affixed to its surface, a ligand which will bind to the characteristic molecule is added to the cell population. The added ligand has fluorescein covalently attached thereto and, hence, the cells to which the ligand has attached (i.e., the desired cells) can be located in areas of the population found to be fluorescent. Suitable, automatic liquid-phase sorters exist which are capable of sorting areas in the population on the basis of the amount or quality of fluorescence. However, the selectivity of these sorters, owing to ever-present background "noise", is such that they are not capable of effective sorting where the desired cells constitute less than about 3% of the number of cells in the population being subjected to sorting. Moreover, these sorters are capable of sorting only up to about 1000 cells per second and, hence, an inordinate amount of time is required to completely scan and sort typical populations containing a large number of cells.

Another method known for isolating cells by virtue of a characteristic molecule which is produced by the cell and becomes affixed to its surface is to flow the cell population over a surface containing a suitable particle or substrate containing a ligand having an affinity for the molecule on the surface of the desired cell. Theoretically, the desired cells will thus be picked out from the flowing cell population by reason of their attachment to the ligand-carrying surface. However, this method of isolation is extremely difficult to perform satisfactorily in practice. On the one hand, if the binding affinity for the ligand to the molecule on the surface of the desired cells is not highly specific or strong, a number of undesired cells also will be captured by the ligand. On the other hand, a high binding affinity between ligand and molecule results in a pinching off of cells in the flowing population and an unwanted retention of desired cells.

SUMMARY OF THE INVENTION

It is an object of the present invention to develop a method for isolating desired cells from a cell population containing these desired cells in mixture with undesired cells.

Another object of the present invention is to develop an isolation method of the type described which has applicability to a wide variety of cell populations and types of desired cells.

Yet another object of the present invention is to develop an isolation method of the type described which can be performed in a relatively uncomplicated, rapid manner.

The attainment of these and other objects will be apparent from the description of the present invention which follows.

In accordance with the present invention, the product produced and released from a desired cell, or the molecule produced by and affixed to the surface of a desired cell, is used, either directly or indirectly, to bring about a unique condition in only the immediate environment of the desired cells in the cell population. The condition preferably constitutes the selective death of all undesired cells in the population, but may also constitute, e.g., selective coloring, fluorescent tagging or insolubilization of either the desired cells or the undesired cells, or areas in their immediate vicinity, so as to pinpoint the location of desired cells in the population.

According to a particular aspect of the present invention, a method is provided for isolating desired cells, which are producing and releasing a particular product, from a cell population containing these desired cells and undesired cells (cells not producing and releasing the particular product). The particular product produced and released from the desired cell may, for example, be an antigen or an antibody. In this method, the particular product may be used directly to shield the desired cell from the lethal action of a drug applied to the entire cell population. Alternatively, the product may be used indirectly to bring about a condition in the cells in the immediate vicinity of the desired cells which causes the cells to protect the desired cells from a lethal environment applied throughout the entire cell population. The particular product also may be used to cause an enzyme to become immobilized near the desired cells, after which the enzyme is used to bring about conditions only in the vicinity of the desired cells. The particular product produced and released from desired cells also may be used to prevent the immobilization of enzyme in the vicinity of the desired cell, after which the enzyme is used to bring about conditions in all areas of the cell population other than where the desired cells exist. Finally, the particular product may be used to bring about the release of an agent only in the vicinity of the desired cells, which agent then brings about particular conditions only in the vicinity of the desired cells.

In another aspect of the present invention, a method is provided for isolating desired cells, which produce and have affixed to their surface a particular molecule, from a cell population containing these desired cells and undesired cells (those not having the particular molecule on their surface). The molecule on the surface of the desired cells may be used to affix an enzyme in the immediate vicinity of the desired cell, after which the enzyme is used to bring about conditions only in the vicinity of the desired cells. Alternatively, the molecule on the surface of the desired cells may be used to bring about the release of a subsequent condition-causing agent only in the vicinity of desired cells.

BRIEF DESCRIPTION OF THE DRAWINGS

FIG. 13 represents an expanded, exposed planar view of an apparatus for isolating cells producing a desired product.

DETAILED DESCRIPTION OF THE INVENTION

The foregoing embodiments of the present invention are explained in detail in the following section with reference to the several figures and particular situations. As will be apparent, many of the considerations and techniques employed in the isolation of desired cells in a cell collection according to the present invention are applicable to some or all of the various embodiments and, where this is indicated to be so, the details of such considerations and techniques are not repeated.

Isolation Of Desired Cells Producing And Releasing A Particular Product

In one aspect of the present invention, the desired cell sought to be isolated from the cell population is one which produces and releases a particular product. This product produced and released from the desired cell (hereinafter referred to as "product") may, for example, be an antigen or antibody or immunoglobulin.

In each of the particular methods for isolating desired cells of this type, use is made of a material (hereinafter referred to as "anti-product") which is capable of specifically binding to the product. For example, where the product is an antibody, the anti-product is the antigen to which the antibody binds at one part of the antigenic determinant. Where the product is antigen, the anti-product is the antibody thereto from a particular species or class. Where the product is immunoglobulin, the anti-product may, for example, be Staphylococcus which binds to the $F_c$ region of the immunoglobulin.

The particular methods for isolating desired cells of this type rely upon the direct or indirect use of the product thereof to bring about certain conditions (or to prevent such conditions from occurring) only in the immediate vicinity of the desired cells. Accordingly, it is essential in these methods that the product, i.e., the product produced and released from a desired cell, exhibit only limited mobility or diffusivity away from the immediate vicinity of the desired cell from which it was released. Appropriate means for achieving this limited diffusivity are discussed later in this description.

Figure 1A:
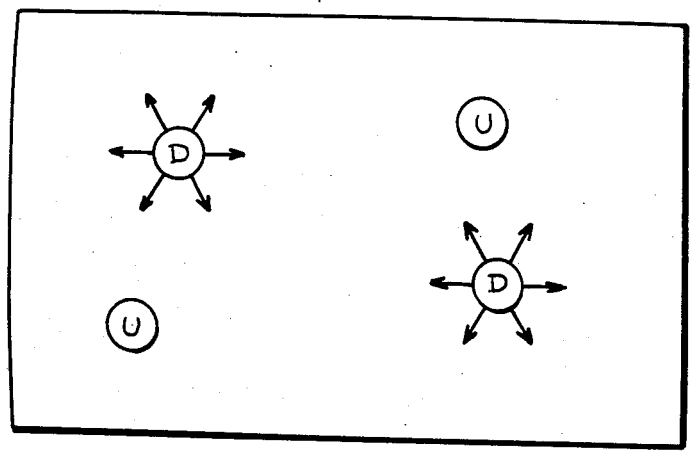
FIGS. 1A and 1B; 2A and 2B; 3A through 3C; 4A through 4C; and 5A through 5D illustrate in diagram form alternative methods for isolating desired cells producing and releasing a particular product.
Figure 1B:
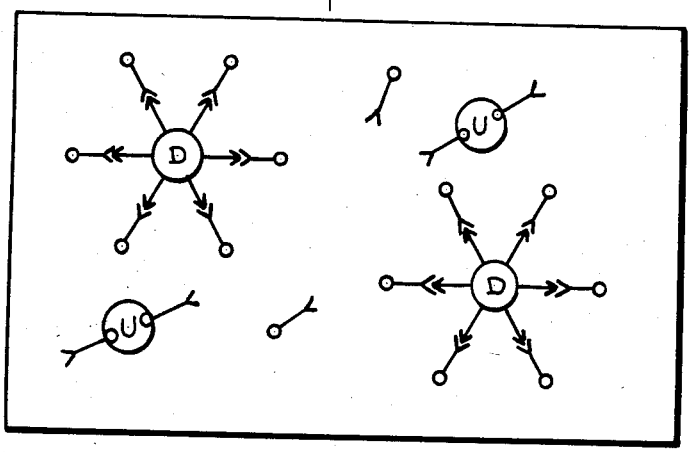

According to a first embodiment for isolating desired cells producing and releasing a particular product, and which is illustrated in FIGS. 1A and 1B, the entire cell population is arranged in a suitable receptacle in which all cells are immobilized in fixed, relative positions and in which the produced and released by the desired cells has only limited diffusivity away from the desired cell.

FIG. 1A illustrates (in greatly expanded scale) the condition of the living cell population after a period of time has elapsed sufficient for the desired cells (D) to produce and release their product (represented by →). Owing to the limited diffusivity of the product by reason of the medium or receptacle in which the cells are placed, the product remains only in the immediate vicinity of the desired cells and cannot migrate to other areas in the population. For this reason also, and in view of the continued production and release of product from the desired cell, the concentration of product is greatest at or near the surface of the desired cell. As is shown in FIG. 1A, undesired cells (U) do not have product at or near their surface since the product is not produced by the undesired cells and since the product cannot diffuse thereto from desired cells.

The next step in the method is to add anti-product to the entire cell population. The anti-product has attached to it by suitable bonding a drug or chemical which will destroy any living cell into which it enters. The condition of the system at this point is shown in FIG. 1B, where anti-product is represented as (>—) and the drug attached thereto is represented as (o). Because anti-product specifically interacts with the product of the desired cells, the drug is prevented from entering into the desired cells by reason of the barrier or shield of product surrounding the desired cells. On the other hand, no such shield exists around the surface of undesired cells; hence the drug/anti-product complex moves unimpeded into the undesired cells and destroys them. As a result, the only cells remaining alive in the entire population are desired cells, and their identification and isolation is achieved.

Figure 2A:
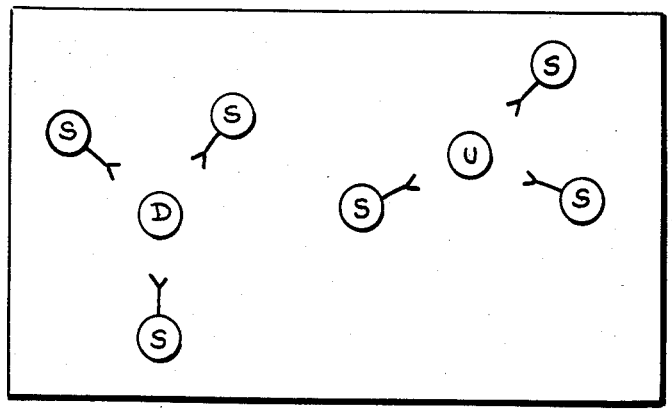
Figure 2B:
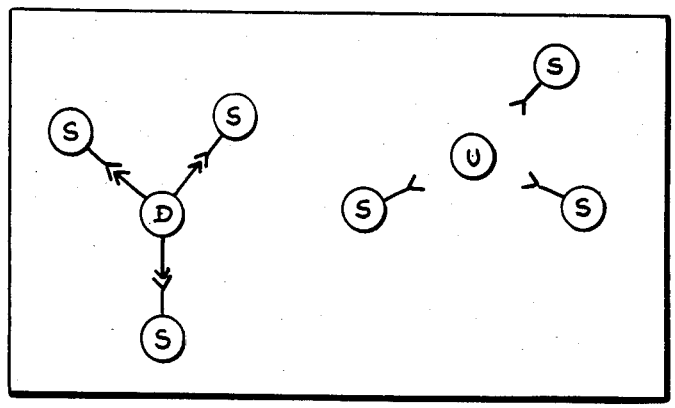

A second embodiment for isolating desired cells producing and releasing a particular product is illustrated in FIGS. 2A and 2B. In this embodiment, the cell population, containing both desired (D) and undesired (U) cells, is arranged in a suitable receptacle along with so-called "scavenger" cells (S). The cells are arranged such that scavenger cells are present throughout the population and essentially surround all desired and undesired cells. Through use of a particular medium or receptacle, the relative positions of all cells are fixed and product produced and released by the desired cells exhibits little or no mobility.

The scavenger cells may be chosen from a variety of cells which exhibit the property that their ability to take up molecules from the environment is significantly increased by reason of alteration of their cell membrane brought about by interaction of product with anti-product (>—) present on the surface of the scavenger cell. In those instances where the product is antibody, one example of such a scavenger cell is tumor cell exhibiting an antigen (anti-product) to which the product antibody can attach. By reason of the attachment, the tumor cell membrane is altered rendering it highly active in taking up molecules ("pinocytosis") from its surroundings. Other cells are capable of the same phenomenon and suitable anti-product (assuming it does not naturally occur on the cell surface) may be affixed thereto by means discussed in further detail hereinafter.

An additional criterion for the anti-product-carrying scavenger cells is that they be chosen such that they eventually will die. For example, the scavenger cells can be irradiated at a level which will allow relatively normal metabolism for a short time (sufficient to perform their scavenging function) before dying. Another example is to employ selected mutant scavenger cells which cannot live in a particular medium.

As illustrated in FIG. 2B, the result of the choice of scavenger cells and their arrangement with the cells of the population is that attachment of product (released from the desired cells) to anti-product on the scavenger cells occurs only in the vicinity where product (→) exists, i.e., only in the vicinity of the desired cells. The next step is to subject the entire population to a noxious (lethal) environment, for example, by addition thereto of methotrexate (4-amino-ptero-glutamic acid) which irreversibly inactivates the cell enzyme, folic acid reductase, which is essential for the cell's production of folinic acid. By reason of the greatly enhanced scavenger function of only those cells whose anti-product has interacted with product (i.e., only those scavenger cells in the immediate vicinity of desired cells), the noxious environment is taken up by the scavenger cells at a rate which prevents the environment from affecting the desired cells. Undesired cells, which are surrounded by scavenger cells which have not interacted with product and which, therefore, do not possess enhanced ability to take up the noxious environment, are killed by the noxious material. After any suitable steps necessary to kill the scavenger cells are taken, the only living cells remaining in the population are desired cells which can, therefore, easily be isolated from the other dead cells of the population.

Figure 3A:
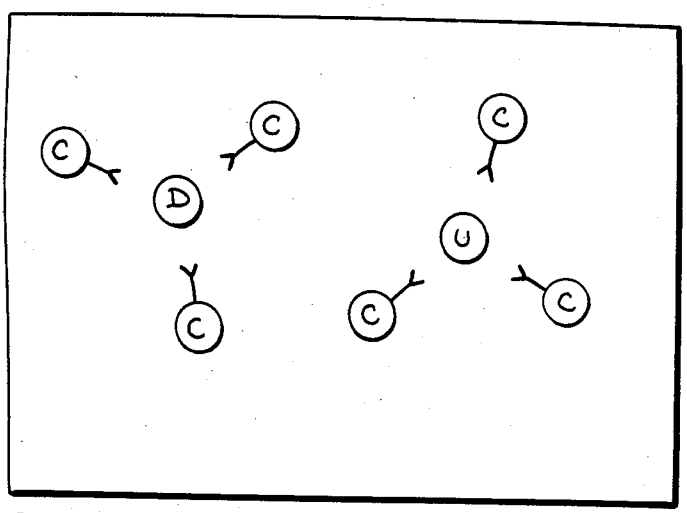
Figure 3B:
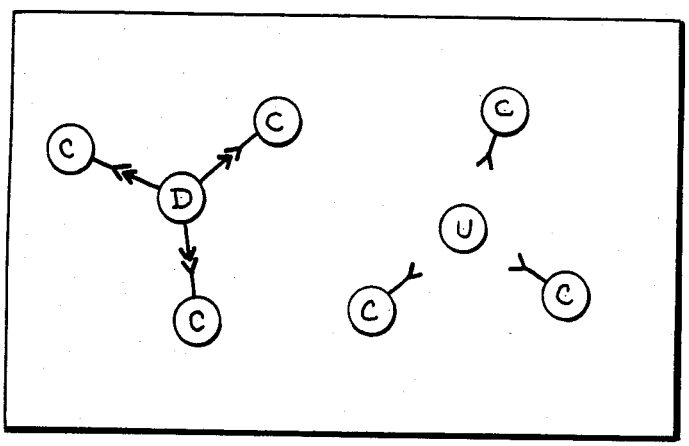
Figure 3C:
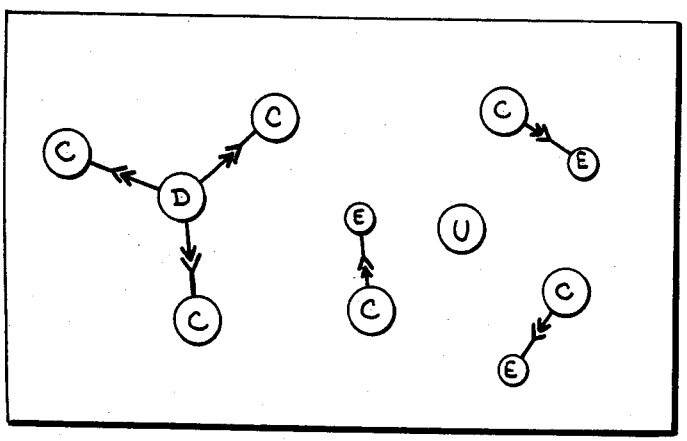

A third method for isolating desired cells producing and releasing a particular product is illustrated in FIGS. 3A through 3C. In this method, the cell population containing desired and undesired cells is arranged in a suitable receptacle or medium along with so-called "carrier" particles or material. The arrangement is such that carrier particles or material (C), which may, for example, be glass beads, red blood cells, liposomes or a gel-like medium, essentially surround all desired cells (D) and undesired cells (U) in the population. The arrangement is such that the cells and carrier maintain fixed relative positions and product produced and released from the desired cells exhibits only limited mobility away from the cell from which it was released.

As shown in FIG. 3A, the carrier has affixed to it a suitable anti-product (>—) which will specifically bind only to the product produced and released from the desired cells. FIG. 3B represents the system after sufficient time has elapsed for desired cells to produce and release product (→). As can be seen, this results in the occupation or tying up with product of all carried anti-product in the immediate vicinity of the desired cells. Since product does not exist in the vicinity of the undesired cells (because product is not made and released by these cells nor can migrate thereto from desired cells), the carried anti-product remains uncomplexed in the vicinity of undesired cells.

The next step in the process is the addition to the entire cell population of what is hereinafter referred to as "anti-(anti-product)" or "anti-AP". Anti-AP is a product which will specifically bind to anti-product. For example, if the product is antigen, the anti-product can be antibody thereto of one species (e.g., mouse) and the anti-(anti-product) can be anti-antibody of another species (e.g., rabbit anti-mouse). The anti-AP has affixed to it through suitable binding an enzyme (E).

The addition to the system of enzyme/anti-AP is illustrated in FIG. 3C. Since the anti-product sites to which anti-AP can bind are fully occupied by product in the immediate vicinity of the desired cell, no fixation of anti-AP (and its carried enzyme) occurs near the desired cell. Anti-AP and its carried enzyme do, however, become bound to the anti-product available for binding in the vicinity of undesired cells. Unbound enzyme/anti-AP may then be removed from the system through a suitable washing.

The foregoing steps result in the presence of enzyme only in the immediate vicinity of undesired cells. As a consequence, it is possible to add to the entire system any suitable material or environment which will undergo enzymatic reaction (in the vicinity of undesired cells) to form some type of state visually or otherwise distinguishable from that which exists where no enzymatic reaction occurs (in the vicinity of desired cells). For example, a colorless material can be added to the system, which material turns to a color in the presence of enzyme. Alternatively, a colored material can be added to the entire system, which material turns colorless in the presence of enzyme. By way of further example, a non-fluorescent material can be added to the system which becomes fluorescent in the presence of the enzyme, or a soluble material can be added which becomes insoluble in the presence of the enzyme. Using any of these techniques, it will be seen that a particular condition can be arranged to occur only in the vicinity of undesired cells by reason of the enzyme being selectively fixed and immobilized only in the vicinity of undesired cells. In this manner, desired cells can be distinguished, and isolated, from undesired cells.

A preferred "condition" caused to exist in the vicinity of the undesired cells is the creation of a lethal environment. Thus, a non-toxic chemical can be added to the entire system, which chemical is converted by the enzyme into a toxic agent lethal to cells in its vicinity (i.e., only the undesired cells). Thus, the only cells remaining alive in the population are desired cells.

Figure 4A:
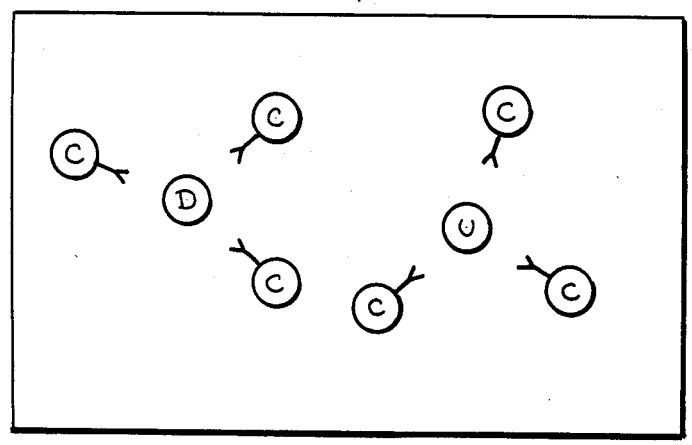
Figure 4B:
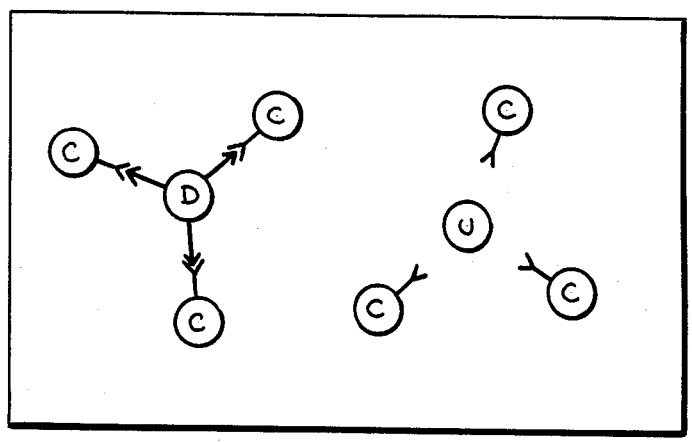
Figure 4C:
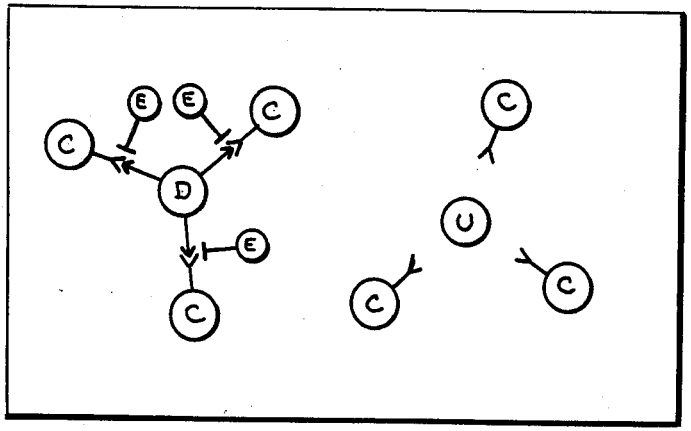

A fourth embodiment method for isolating cells producing and releasing a particular product is illustrated by FIGS. 4A through 4C and is similar in many respects to the preceding embodiment. In this method, however, enzyme is caused to be immobilized only in the vicinity of desired cells rather than in the vicinity of undesired cells.

As shown in FIG. 4A, the cell population once again is arranged, with carrier particles or carrier material to which anti-product has been appended, in a manner such that the relative positions of the cells and carrier are fixed and little or no migration of product released from desired cells occurs. After a suitable time period, shown in FIG. 4B, product from a desired cell will become affixed to the anti-product on the carrier particles surrounding the desired cell. No such attachment occurs in the vicinity of undesired cells since no product exists in that vicinity.

The next step (FIG. 4C) is to add to the entire system a material which will bind specifically only to product or the complex of product or anti-product. This "anti-product$_2$" may, for example, in the case where the product is immunoglobulin and the anti-product is Staph., be anti-immunoglobulin which can bind to $F_C$ or $F_{AB}$ regions of the immunoglobulin. The anti-product$_2$ has affixed to it an enzyme (E). As a result, the enzyme/anti-product$_2$ complex ( E —|) will become affixed only where product or the interaction of product and anti-product exists, i.e., only in the vicinity of desired cells.

After removing unbound enzyme/anti-product$_2$ from the system, the system can be subjected to any of the previously mentioned environments to yield a colorimetric, fluorescence or insolubilization indication, through the action of the enzyme, of the location of desired cells. Alternatively, the system can be subjected to a toxic environment which is detoxified by the enzyme only in the vicinity of the desired cells so as to arrange that the only cells remaining alive in the population are desired cells. In a somewhat similar technique, the entire system may be subjected to an environment lethal to all the cells (e.g., via the addition of methotrexate). The methotrexate is then washed from the system and folic acid is then added to the entire cell arrangement. The enzyme previously immobilized only in the vicinity of desired cells is chosen as one capable of converting this otherwise inert folic acid into folinic acid which brings about a revival only of the cells in its vicinity, i.e., the desired cells. An enzyme suitable for such purpose is folic acid reductase.

A fifth embodiment method for isolating cells producing a particular product is illustrated in FIGS. 5A through 5D. As in previous discussed methods, the cell population is arranged, together with carrier particles carrying anti-product, in a manner such that the relative positions of the cells and carrier particles are fixed and the migration of product away from the desired cells from which it is released is inhibited.

In this embodiment, the carrier particles contain within their interior a so-called "encapsulated agent" which, for purposes of present discussion, is taken to be an enzyme. This encapsulated agent is introduced into the carrier particles, during manufacture (where the carrier is, e.g., liposome) or, where the carrier is red blood cells, by osmotically causing the cell to swell in a hypotonic solution containing the agent (enzyme) to permit the cell to take up the enzyme, and then causing the cell to contract to its original size by returning the solution, containing the red blood cells, to normal tonicity. As in previous embodiments, the cell population and anti-product carrying, enzyme-containing carrier particles are arranged so as to insure that all desired and undesired cells in the population have carrier particles in fixed proximate, preferably contiguous, relation thereto (see FIG. 5A).

Figure 5B:
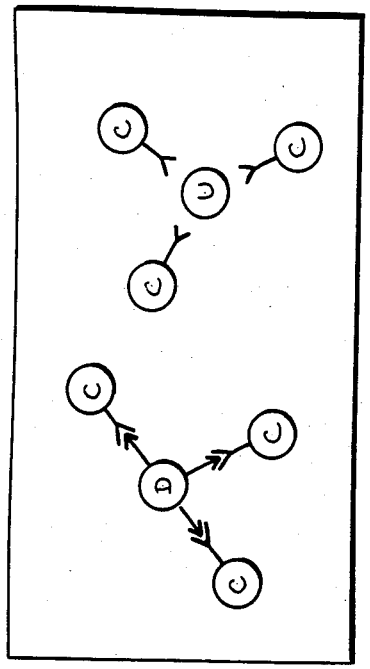
Figure 5D:
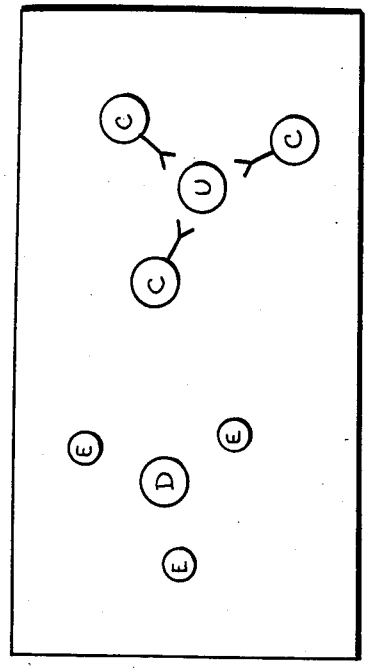
Figure 5A:
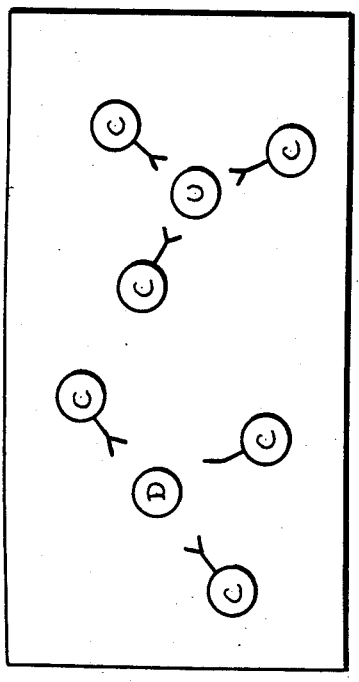
Figure 5C:
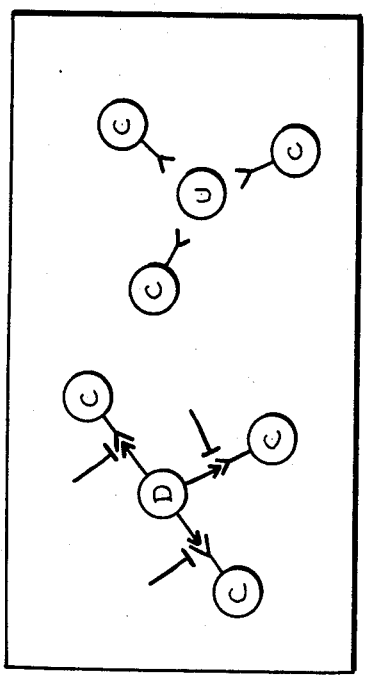

After a suitable incubation period, product released from desired cells will bind to anti-product on the carrier particles in the vicinity of the desired cells (FIG. 5B). No such attachment occurs in the vicinity of undesired cells since product does not exist in this vicinity.

According to a particular method within this embodiment, the next step (FIG. 5C) is the addition to the entire system of a material (—|), which attaches only where a product/anti-product complex exists (much like the anti-product$_2$ discussed earlier) and which, by virtue of such attachment, causes the red blood cells or liposomes carrying this complex to rupture. An example of such a materal is complement. The rupture of these complex-carrying red blood cells or liposomes (which exist only in the immediate vicinity of the desired cells) causes the release therefrom of the enzyme encapsulated therein. Because the system is arranged so that cells, carrier and product are immobilized and released encapsulated agent is either immobilized or has very limited ability to diffuse, the enzyme (E) released from the ruptured carrier becomes concentrated in the vicinity of its release, i.e., in the vicinity of the desired cells. See FIG. 5D.

With the enzyme now concentrated in the immediate vicinity of the desired cells, the various procedures earlier discussed for using the enzyme to create a distinguishable state only in the vicinity of the desired cells may be employed. For a given, pre-determined enzyme, the system can be arranged to color (or remove color from) only the area in the vicinity of the desired cells and/or to insolubilize the color only in this area or to cause only this area to be fluorescent or to detoxify an otherwise toxic agent only in this area or to rescue only cells in this area from a noxious environment.

According to another particular method within this embodiment, the encapsulated agent may be a material which directly rescues the desired cells from a noxious environment. For example, the system, prior to the addition thereto of the material which attaches to the product/anti-product complex, can be subjected to methotrexate which will cause all desired and undesired cells in the system to begin to die. The methotrexate is then washed from the system and the material which attaches to the product/anti-product complex is added. The rupture of red blood cells or liposomes resulting from this attachment causes there to be released (only in the vicinity of the desired cells) a chemical, such as folinic acid, which was encapsulated within the red blood cells or lipsomes, which is capable of rescuing the desired cells from the death process.

In the preceding embodiment, it may be desirable to append to the encapsulated agent (e.g., the enzyme or rescue chemical), which is contained in the red blood cell or liposome, an inert macromolecule which inhibits any natural, spontaneous release of the agent from the red blood cell or liposome prior to the time the blood cell or liposome is destroyed or ruptured by, e.g., the action of complement. Natural or spontaneous release of the agent, if substantial, will result in the presence of enzyme or rescue chemical in the vicinity of cells other than the desired cells. In general, natural or spontaneous release of materials from liposomes is very small and will not warrant use of a natural release-inhibiting macromolecule. Apart from inhibiting the natural release of enzyme or rescue chemical prior to red blood cell or liposome rupture, macromolecules attached to the enzyme or rescue chemical also will desirably limit diffusion of the enzyme or rescue chemical from the ruptured cell or liposome so as to insure that only cells in the immediate vicinity of the rupture (i.e., desired cells) will have enzyme or rescue chemical available to them. Normally, however, the geometrical arrangement of the system itself will be sufficient to insure this condition.

In each of the foregoing embodiments, it is necessary to arrange the cell population (and, if applicable, any carrier particles) in a manner such that the cells in the population (and, again, any carrier particles) are essentially immobilized in fixed positions. The system also must be arranged such that product produced and released from the desired cells does not migrate away from these cells to any substantial degree because the effectiveness of the various methods for causing conditions selectively to occur or not occur only in the immediate vicinity of desired cells depends upon limiting the interactions of product to the immediate vicinity of the desired cells. Still further, in those embodiments where agents or materials are released into the system, migration of these materials away from their point of release similarly must be minimized.

Figure 6A:
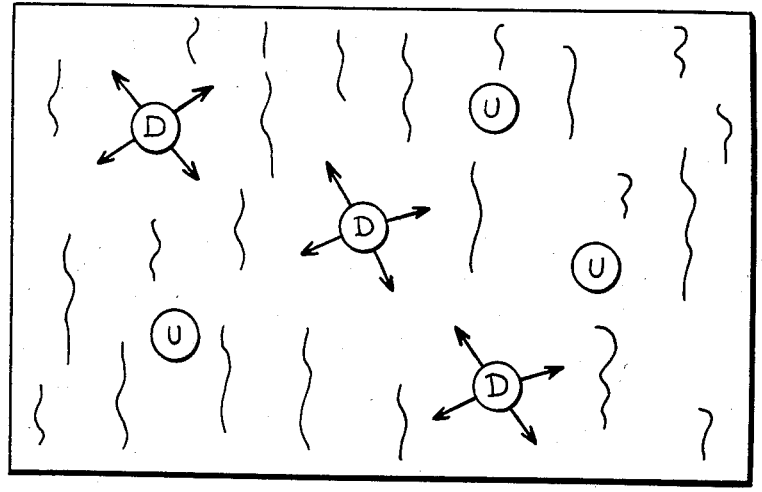
FIGS. 6A and 6B represent an illustration of a gel-based arrangement for immobilizing cells and products.
Figure 6B:
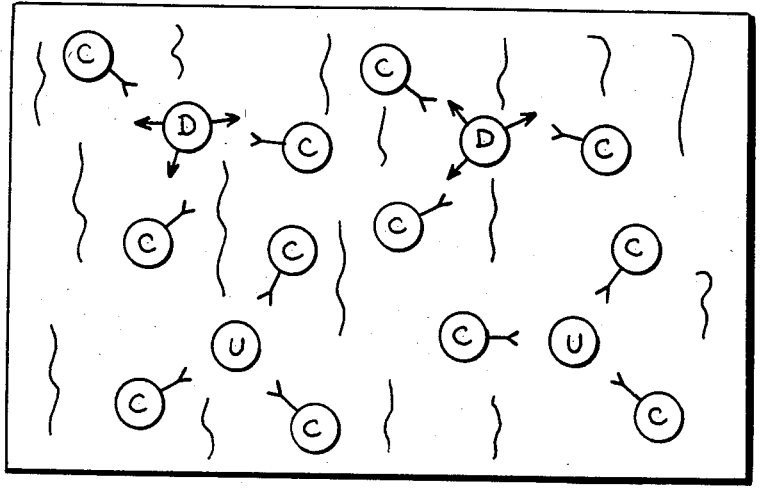

To achieve these conditions, a number of techniques are available. In one such technique, illustrated in FIG. 6A, the cell population is arranged in a gel medium such as agar, agarose, alginate, collagen, nitrocellulose or gelatin which fixes desired (D) and undesired (U) cells in fixed positions and limits diffusion of product away from desired cells. Where carrier particles are employed (see FIG. 6B), these same gel materials may be employed to fix the positions of desired cells, undesired cells and carrier (C) and to limit the migration of product and any material released from the carrier. Alternatively, in embodiments wherein anti-product is affixed to carrier, the gel itself may constitute the carrier for anti-product.

Figure 7:
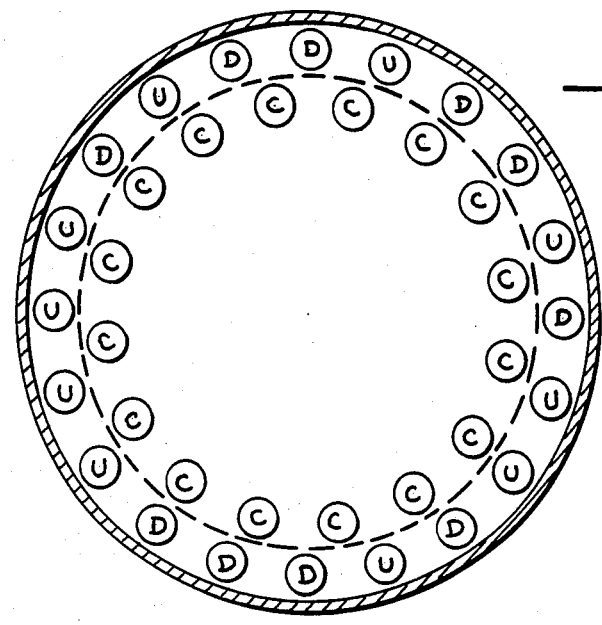
FIG. 7 represents a top, exposed view of a centrifuge interior for immobilizing cells and products.

An additional method for achieving this immobilization employs a centrifuge to maintain the cell population in a thin, single-cell layer against a surface of the rotating centrifuge. As shown in FIG. 7 for the case where carrier particles (C) are employed, the cells in the population, including desired cells and undesired cells, are maintained against the inner surface of a rotating centrifuge. A layer of filter paper containing fixed carrier particles is in contact with the thin cell population layer. The forces resulting from the centrifugal motion maintain the cells in the thin cell layer and the particles in the filter paper in fixed relative position such that interactions caused by the proximity of desired cells and anti-product-carrying particles may be used as a means for identifying the location of desired cells.

Figure 8:
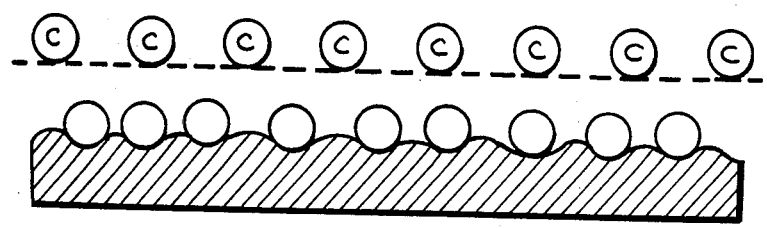
FIG. 8 represents a side view of a stippled surface for immobilizing cells and products.

Another method for achieving the required immobilization is the utilization of a vessel (see FIG. 8) having a surface which has been microscopically stippled such that the cells in a cell population occupy substantially individual and fixed positions when added to the vessel. Again, for the case where anti-product-carrying carrier particles are used, a material such as filter paper is employed to contact the cells with anti-product-carrying particles or material in fixed position in the filter paper.

Figure 9A:
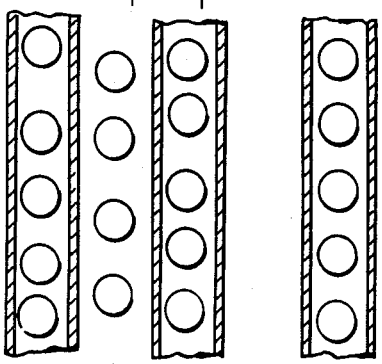
FIGS. 9A and 9B represent side views of a hollow fiber arrangement for immobilizing cells and products.
Figure 9B:
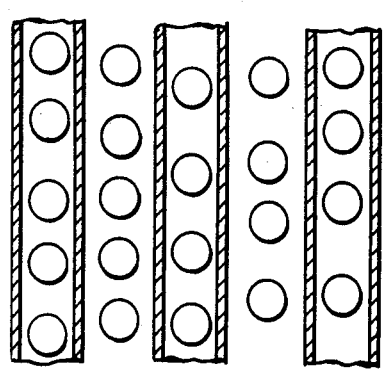

Yet another method for achieving immobilization is to place the cell population (including desired cells and undesired cells) inside or outside of hollow fibers, as shown in FIGS. 9A and 9B. The hollow fibers are made of permeable membrane material which is sized so as to permit product from desired cells to interact with anti-product-carrying particles (which are fixed in position either inside or outside the hollow fibers as the case may be) while preventing cells or carrier particles from passing through the membrane pores.

In connection with the foregoing embodiment methods for isolating desired cells producing a particular product, a number of instances occur where materials must be affixed to one another before use in the method. For example, in certain embodiments it is necessary to bind enzyme either to anti-product or anti-AP or anti-product$_2$, and this may be accomplished through known covalent binding techniques or through natural coupling where antibody to the enzyme is made, coupled to the enzyme by natural affinity and the anti-product or anti-AP or anti-product$_2$ is then chosen to be one which itself has affinity for the enzyme antibody or the enzyme/antibody complex. Techniques also are known for achieving the requisite coupling of chemicals or drugs to, e.g., anti-product of various types.

In the case where anti-product carried by a carrier particle is required for a particular method, a number of methods are known for obtaining these particles. By way of example, and for the case where the product is antibody, the carrier particle is a red blood cell or liposome and the anti-product to be carried by the red blood cell or liposome is antigen, the following methods may be employed:

(a) attaching the antigen to the surface of the red blood cell or liposome covalently through chemical attachment without killing or severly injuring the red blood cell or lipsome;

(b) incubating the red blood cells or liposomes with the antigen to bring about adsorption of the antigen on the surface of the cells or lipsomes. This also can be accomplished by culturing red blood cells or lipsomes with an organism (such as trypanasomes) which releases the antigen into the culture meduim for attachment to the cells or liposomes;

(c) utilizing bridging means whereby the antigen is attached to a molecule, such as a fatty acid, e.g., palmytolic acid, which has a high natural affinity for cell or cell-like membranes;

(d) for red blood cells, incorporating the antigen onto or within a liposome which has a natural tendency to fuse with cell membranes and to deposit the products of the liposome onto the cell surface membrane;

(e) incubating cells which have receptors for complexes with complexes (or fluid containing complexes) of the antigen and antibody. The complexes attach to the cells through the Fc region of the antibody. If the antigen is multi-valent, and the complex is in the region of antigen excess, the attached complex will have free antigen available for attachment to the specific antibody being produced by the desired cell;

(f) inducing the cells to have the antigen on their surface. This can be accomplished by infecting the cell with an organism (e.g., virus or parasite) whose antigen becomes part of the surface of the cells, or which induces the cell to make a specific antigen;

(g) attaching antigen to the surface of a red blood cell or liposome by fusing to these materials membrane fragments or bits obtained from a cell containing the antigen; and (h) where the product being produced by the desired cell is antibody, and the anti-product is antigen, the carrier particle can be a living cell, e.g., a tumor cell, inherently containing the particular anti-product, e.g., tumor antigen.

Isolation Of Desired Cells Having A Characteristic Molecule On Their Surface

In accordance with another aspect of the present invention, methods are provided for the isolation of desired cells which produce, but do not release, a product. Rather, the "product" becomes affixed to or a part of the surface of the desired cell. This product or molecule, characteristic of the desired cells sought to be isolated, can be used in a manner similar to that earlier described to cause particular conditions to occur (or not occur) only in the vicinity of the desired cells.

An important distinction from the methods earlier discussed, where product is released from desired cells, is the fact that here product remains on the surface of the desired cells and cannot migrate away from the desired cells. As a result, the interaction between product and other materials which is used as the basis for the isolation of desired cells of this type, always occurs either on the membrane surface of the desired cell or in the immediate vicinity of the desired cell. Hence, means for immobilizing cells and for limiting migration of product from desired cells is not strictly required.

Another distinction resides in the fact that in many cases the use of anti-product is not required in order to direct a material (e.g., an enzyme) specifically to the vicinity of a desired cell. Rather, the enzyme may be directly affixed to the product on the desired cell surface through choice of appropriate antibody.

Given those considerations, a first embodiment method for isolating desired cells having a characteristic molecule or product on their surface involves simply the addition to the cell population (e.g., in a stirred vessel or suspension) of an enzyme capable of specifically binding only to the product on the surface of the desired cell. With the enzyme now in place only in the vicinity of (actually, affixed to) the desired cell, the various conditions earlier described which can be brought about by the enzyme so as to selectively distinguish desired cells from undesired cells may be employed.

It will be appreciated that this same result can be brought about through use, if desired, of anti-product, etc. as described ealier for cells producing and releasing product. Thus, anti-product may be used to bind to the product on the cell surface and anti-product$_2$, which selectively binds either to product or product/anti-product complexes, to which enzyme is attached, can be used to direct the enzyme only to the vicinity of the desired cell.

In another embodiment for isolating desired cells having a characteristic molecule or product on their surface, a technique similar to that shown in FIGS. 5A through 5D may be employed wherein a carrier having anti-product thereon and in which an encapsulated agent is contained (e.g., enzyme or rescue chemical) is bound to product on the desired cell surface, after which a suitable agent is used to rupture only the carrier particles on which product/anti-product interactions have occurred. The rupture of the carrier releases enzyme or rescue agent only in the vicinity of the desired cell (assuming a migration-inhibiting arrangement is employed).

DESCRIPTION OF PREFERRED EMBODIMENTS

Within the context of the foregoing description, certain methods and procedures are, at the present time, considered to be particularly preferred.

With respect to the required immobilization of the cells and other materials in order to insure that interactions between the product produced by a desired cell and some other material will either directly or indirectly cause a condition to occur (or prevent a condition from occurring) only in the vicinity of a desired cell, a preferred immobilizing technique involves the "encapsulation" of single cells within a solid or hollow bead-like material, e.g., a bead made from agarose, alginate, gelatin, etc. This immobilizing technique is applicable for use with any of the isolation methods discussed earlier.

The object of immobilization in this manner is to provide integral, separate beads, each containing a single cell from the cell population, be it a desired cell producing a desired product (e.g., antibody) or an undesired cell. This can be accomplished using generally known techniques for making micro-beads of a uniform size, wherein the cell population is suspended in a sufficient amount of bead-forming material such that, statistically, bead formation will result in the presence of a single cell therein. Bead formation is accomplished by, e.g., emulsifying the suspension in an oil at a temperature or under conditions at which the bead forming material is liquid and then slowly altering the conditions (e.g., cooling) such that bead formation occurs and beads separate out from the emulsion.

Where the isolation method employed is one which depends upon the presence of other particles near or around the cell, for example, scavenger cells (FIG. 2), carrier particles (FIGS. 3 and 4) or carrier particles containing an encapsulated agent (FIG. 5), the bead formation can be arranged such that one or more of these materials or particles are encapsulated along with a cell from the cell population within the bead.

The beads formed are such that the various materials required for the isolation techniques discussed earlier, e.g., anti-product plus drugs or enzymes or anti-AP or anti-product$_2$ with affixed enzymes, rescue chemicals, noxious environments, fluorescent materials, etc. all can freely enter the bead for interaction with the cells therein and can freely be washed from the beads where no binding interaction has occurred. At the same time, of course, the bead porosity is such that the cell or other particles encapsulated therein cannot escape.

By way of example, use of this immobilization technique may be illustrated with reference to the isolation method generally depicted in FIG. 3. The beads are prepared such that each contains a single cell, be it a desired cell or an undesired cell, together with one or more particles carrying anti-product. As opposed to the situation depicted in FIG. 3, i.e., wherein desired and undesired cells are present (albeit in immobilized condition) in the same medium or apparatus, the use of beads results in the physical separation of one cell from the other.

After a suitable incubation period, product from the desired cell affixes to anti-product on the carrier, while, in beads where there are no desired cells, the anti-product on the carrier remains uncomplexed. Thereafter, anti-AP plus enzyme is added to the entire bead collection. The anti-AP plus enzyme diffuses into all the beads but only becomes affixed in those beads having uncomplexed anti-product, i.e., those beads containing an undesired cell. After washing away non-affixed anti-AP plus enzyme, the entire system of beads may then be subjected to any of the number of possible environments which will undergo a measurable or distinguishing change in the presence of enzyme, i.e., only in the beads containing an undesired cell. For example, the environment may be such as to be enzymatically converted to a colorless or colored condition or a fluorescent condition or a lethal condition, etc.

As will be appreciated, the fact that the desired cells, when eventually selectively distinguished in some manner from the undesired cells (e.g., by coloration or fluorescence or by the mere fact that they are living), are contained in beads makes their isolation from the undesired cells, also contained in beads, potentially more difficult. For example, if the isolation technique relies upon arranging that the desired cells selectively survive (or are not exposed to) a lethal environment which kills all undesired cells, it still is necessary to isolate those beads containing the living (i.e., desired) cells. For this reason, a number of alternative techniques have been developed for particular use with bead immobilization.

In a first such method, utilizing previously-discussed techniques wherein enzyme is selectively affixed in the vicinity of (i.e., within the bead containing) either a desired cell or an undesired cell, the enzyme can be chosen such that, after a brief time after such affixation, it is capable of directly or indirectly dissolving the bead material thereby selectively leaving beads containing desired or undesired cells, as the case may be, intact. In one embodiment of this method, alginate is used as the gel material for forming the bead. After enzyme is selectively affixed to or near particular cells within beads, the beads are individually surrounded by a porous low molecular weight cut-off layer, e.g., a lipid material. The enzyme is chosen such that it hydrolyzes the alginate material. After hydrolysis, calcium ions are removed from the entire system (e.g., through washing or through addition of a suitable sequestering agent) thereby causing the alginate gel (which depends on calcium for its gelling properties) to become liquified. The surrounding porous layer is chosen to have a porosity such that the liquified gel cannot pass through the layer but which does permit the enzyme-hydrolyzed gel material to escape from the layer. After removing this escaped material, the entire system is recalcified, causing the alginate to gel. Upon removal of the outer surrounding layer, the system consists of gelled beads containing, as the case may be, only desired or undesired cells.

A second method for accomplishing isolation of particular beads is to choose an enzyme (for selectively affixing in beads containing desired or undesired cells, as the case may be) which is capable of comverting a particular envirnoment into one which physically differentiates from beads in which the environment is not so converted. An example of this method is to utilize an enzyme which will cause an environment to release oxygen or other gaseous materials sufficient to establish a density differential capable of, e.g., levitating the beads in an aqueous system to a level higher than achieved by beads where no such conversion occurs. Thus, using catalase as the enzyme, hydrogen peroxide may be added to the system for conversion to hydrogen and oxygen which causes the beads in which such conversion occurs to levitate above those where no gas is produced. At the same time, of course, the hydrogen peroxide, where unconverted by catalase, will be lethal to cells in the beads. Hence, in this particular embodiment, the selective affixation of catalase enzyme is arranged to be in beads having desired cells, e.g., by a method similar to that illustrated in FIGS. 4 and 5.

A third method for isolating particular beads is by arranging that, under the influence of enzyme or other material, only the beads containing desired cells remain gelled in the system. This can be accomplished by a number of procedures.

In one procedure, for use where the product of the desired cell is antibody, the antigen thereto can be incorporated directly onto the gel material from which the bead is made. In addition to capturing antibody from the desired cell, the antigen will cross-link the gel material after a suitable period of time. Thus, as in a method discussed earlier, all the beads can be surrounded by a barrier layer. Using alginate gel as an example, calcium is removed from the system, causing the gel to liquify. The liquified gel plus antigen (to which antibody has not affixed, i.e., from beads containing undesired cells) diffuses through the barrier layer, by choice of a suitable porosity therefor, and is removed from the system. Liquified gel where antigen has complexed with antibody cannot diffuse through the barrier. Thereafter, the gel is recalcified and, after removal of the barrier layer, all that remains are gelled beads containing desired cells.

Another procedure useful in this regard is to include within the beads containing desired and undesired cells so-called "micro-capsules" containing calcium sequestering agents and calcium-containing agents. Thus, where the bead is made of alginate, the microcapsules may be liposomes containing the noted products. Using an isolation technique wherein enzyme is selectively affixed in the vicinity only of desired cells (i.e., within beads containing desired cells), a barrier layer is thereafter used to surround each of the beads in the system, i.e., those containing desired as well as undesired cells. By raising the temperature of the system, the liposome (within all the beads) which contains a calcium sequestering agent (e.g., EDTA) is caused to burst. The EDTA removes or binds up calcium ions from the gel and causes the gel to liquify. The barrier is chosen such that liquified gel cannot diffuse through the barrier. The second liposome within the bead, which carries calcium ions (e.g., calcium salts), is chosen such that it is degraded by the enzyme used in the affixing step. Since this enzyme exists only in beads which contain desired cells, calcium will be released only in these beads and will cause the liquified alginate to gel. When the barrier layer is removed and the system washed, the only solid particles remaining are the gelled beads which contain desired cells.

Another procedure for arranging that only beads containing desired cells remain intact, is to include within all beads a microcapsule containing a product which cross-links the gel material of the bead and which is only released from the microcapsule in the presence of enzyme material. For example, where agarose is the gel material making up the bead, the microcapsule can contain an "antibody" against the agarose molecules which, upon binding thereto, cross-links the agarose. Using the barrier layer earlier discussed which will permit only liquified agarose to which no antibody is attached to diffuse out from the layer, the entire system may then be subjected to a condition which will liquify all agarose gel. The liquification of the gel permits the enzyme to act upon or digest the microcapsules to permit them to release their product (cross-linking agent). Upon re-gelling the agarose and removing the barrier layer, all that remains are gelled beads containing the desired cells.

Alternatively, the microcapsule may contain "antibody" to a material affixed to the agarose (rather than the agarose per se), for example, agarose to which hapten has been affixed.

In yet another procedure, a barrier may be used which does not permit any liquified gel to escape. After the microcapsules have been digested, releasing, e.g., antibody which cross-links the gel, removal of the barrier results in the release of all material in the system except desired cells in cross-linked gel.

Utilization of the bead immobilization technique also permits the use of a so-called "amplified" response in isolating cells according to any of the methods of the present invention.

According to this amplification procedure, in any situation where an enzyme is required to act upon the entire bead the system is arranged such that enzyme-disruptable microcapsules within the bead are used to provide the material which acts upon the bead. The reason for operating in this manner is that the total amount of enzyme which can be brought to bear on a given bead is very small by reason of the fact that the amount of enzyme present is directly proportional to the amount of product produced by the desired cell, since it is this product which, either directly or indirectly, causes the selective affixing of enzyme at desired cell sites. Since the amount of product produced by a desired cell is quite small, the concomitant small amount of enzyme possibly may not be sufficient to act upon the entire volume of the bead. However, the amount of enzyme generally is sufficient to act upon (i.e., digest) the relatively thin surfaces of microcapsules within the beads, which microcapsules release a sufficient quantity of products which then act upon the entire bead volume. In this manner, the "response" of the bead to small amounts of enzyme is greatly amplified. Moreover, the use of many small microcapsules rather than a few large microcapsules, the sum of which small capsules contain the desired quantity of material (e.g., color, rescue material, EDTA, calcium salts) to be released, enables a small quantity of enzyme to be even more effective in rupturing the capsules, since smaller capsules have thinner and more easily ruptured surfaces. In this manner, greatly intensified or amplified reactions can be achieved from only small quantities of product from desired cells.

In another form of amplification, an enzyme can be used to convert an antigen of one type to antigen of another type, which second antigen may then be captured by antibody affixed to liposomes (after which the liposomes may be lysed, e.g., via complement) or by antibody on the gel material of the bead, thereby greatly amplifying the number of liposomes or antibody sites on the gel which can be acted upon. A somewhat related procedure, employing no enzyme, is illustrated by the following specific embodiment. Thus, in all beads, i.e., those containing a desired antibody-producing cell or an undesired cell not producing desired antibody, there is included product, anti-product, and anti-AP or anti-product$_2$ attached to an antibody to the virus phage or to an antibody to a hapten which is fixed to the phage. After washing, the anti-AP or anti-product$_2$ plus anti-phage (or anti-hapten) remain only in beads containing desired cells. Another gel bead is then used to surround each first bead, and in this surrounding bead layer is placed phage and a bacteria which, when growing, produces large quantities of products which can attach to and cross-link gel material of the bead or which can attach to antibody thereto on liposomes within the first bead. The anti-phage is split from anti-AP or anti-product$_2$ in the first bead and diffuses into the surrounding gel where it inactivates phage. Since the bacteria will only grow where no living phage exists, the bacteria will grow, and release products, only in beads containing desired cells. The products released by the bacteria, which are of enormous quantity, then diffuses into the first bead to act on antibody thereto either affixed to gel or liposomes. In this manner, a large quantity of material is brought to act upon the bead.

In connection with these amplification techniques or other techniques described herein where enzyme is used to breakdown microcapsules (made, e.g., of lipid material) and thereby cause the microcapsules to release a particular agent (e.g., gel cross-linking agent, calcium ions, coloring material, etc.) it is desirable to provide that the enzyme freely travels within the bead to the location of the microcapsules. This is so because the enzyme, which when added to the beads is complexed to anti-product$_2$ or anti-AP and which thereafter becomes affixed to product or product/anti-product complexes within the beads, is relatively immobilized within the bead. While in some cases the immobilized enzyme is of sufficient strength or sufficiently proximate to the microcapsules to act thereupon, it is preferred to arrange that the enzyme become "mobile" so as to insure its intimate interaction with microcapsules. This can be accomplished in a number of ways. Thus, in one such method, the previous linking of the enzyme to anti-product$_2$ or anti-AP can be performed via any reversible cross-linking agent, e.g., disulphide linkages. After the enzyme/anti-AP or anti-product$_2$ complex has become affixed in the bead by reason of its interaction with product from a desired cell in a bead, suitable agents may be introduced which split the bond and release the bound enzyme to migrate throughout the bead. In another method, the anti-product$_2$ or anti-AP to which enzyme is attached can be chosen such that it has a sufficient, yet low, binding affinity for product or product/anti-product complexes. After the enzyme/anti-product$_2$ or anti-AP complex is affixed to product or product/anti-product, anti-product$_2$ or anti-AP having a high binding affinity for product or product/anti-product is added to the system. This high affinity material displaces the enzyme/anti-AP or anti-product$_2$ complexes previously in place and thus permits the enzyme (with its attached anti-AP or anti-product$_2$) to migrate throughout the bead to interact with microcapsules.

The use of enzymes to break-down liposome microcapsules typically entails a somewhat slow process, which is desirable since otherwise premature release of the microcapsule contents would occur simply upon introduction of enzyme/anti-AP or enzyme/anti-product$_2$ complexes to the beads. In order to insure, however, that such premature release does not occur (e.g., where the enzyme activity is very rapid and/or where the products of the enzymatic degradation of the liposome would be harmful to the cells per se), certain procedures may be employed.

In one such procedure, enzymes are chosen which do not act upon the liposomes or other microcapsules unless in the presence of an activator (e.g., co-factor) which is not added to the system until after the enzyme/anti-AP or enzyme/anti-product$_2$ has become affixed within a particular bead. Alternatively, the liposome and enzyme can be chosen to be active only above particular temperatures, and the temperature is not raised until after enzyme/anti-AP or anti-product$_2$ complexes have been affixed in a particular bead. An additional procedure is to surround each microcapsule with, e.g., an agarose layer or capsule of low permeability and through which enzyme/anti-AP or enzyme/anti-product$_2$ cannot diffuse to act upon the liposomes or groups of liposomes. When, using methods earlier described, enzyme is split off from the complex to migrate throughout the bead, it is now of a size which will permeate the agarose layer and act upon the liposome therein. In this procedure, it may be useful to combine the feature that the enzyme activity on the liposomes is temperature dependant. Raising of the temperature of the liposomes can be achieved by raising the temperature of the entire system or by induction heating, where a small metal particle is incorporated in the agarose layer which contains the liposome.

In a particular embodiment utilizing principles similar to those earlier described, liposomes are employed which have appended to their surface an antibody to penicilloic acid. The enzyme added to the system (complexed with anti-AP or anti-product$_2$) is penicillinase. After affixing the enzyme complex within the bead, penicillin attached to a carrier material is added to the system. The penicillinase enzyme converts the penicillin to penicilloic acid and the penicilloic acid plus carrier is then captured by the antibody affixed to the liposome surface. An antibody to the carrier is then added and, thereafter, the addition of complement to the system will lyse the liposome and release the products contained therein.

In another specific embodiment, urokinase is chosen as the enzyme affixed to anti-product$_2$ or anti-AP. After the enzyme becomes affixed and immobilized in beads containing desired cells, plasminogen, a soluble, essentially inactive material, is added. The plasminogen is converted by the immobilized urokinase into the soluble, active proteolytic enzyme plasmin. By using microcapsules made of polylysine to contain the products (e.g., gel cross-linking agents) which act upon the bead, the plasmin digests these microcapsules and the products are thereby released. In this embodiment, therefore, it will be seen that it is not strictly necessary that the enzyme be freed to work upon the bead or liposomes within the bead.

In all the isolation techniques of the present invention, be they performed in any of the immobilization modes discussed herein (e.g., hollow fibers, gels, centrifuge surfaces, beads, etc.), a particularly preferred method (described for beads below) for isolating desired cells producing and releasing a desired product includes affirmative steps designed to isolate only those desired cells making a particular desired product.

Thus, in isolation techniques described herein where "antigen" which possesses a large number of antigenic determinants, each capable of binding a different antibody, is used to capture "antibody" from many clones, each growing in a separate bead, where it is desired to isolate a cell or clone making a particular antibody (e.g., a hybrid cell making a particular monoclonal antibody), a method is used to inhibit the antigen from capturing other, undesired antibodies, such as those which have been made before. In this method, when antigen is added to the system, there also is added at least one, and ideally all the repertoire of, antibodies (the $F_{AB}$ fragment thereof) produced by all other antibody-producing cells other than the desired cells making and producing the desired antibody. By thus occupying all undesired antigenic binding sites by the addition of the undesired antibodies (as the $F_{AB}$ fragment, which does not contain $F_c$ region), the multi-valent antigen will only capture desired antibodies (which do contain $F_c$ region) produced and released from the desired cells. Thereafter adding enzyme coupled to anti-$F_c$ will affix enzyme only in the vicinity of the cells producing desired antibody or antibodies other than those added to the system.

A similar technique may be used employing antigen to achieve this selective capture of particular antibodies. Thus, for example, in a bead containing an antibody-producing cell there may be added antigen to one or more of the antibodies produced. In a second layer around the bead may be placed the antigen to the desired antibody. Antibody other than the desired antibody will remain within the first bead since it becomes complexed with antigen therein. Desired antibody is free to diffuse to the second layer where it is bound to its antigen.

Among the most preferred methods for isolating a desired cell, making a desired product, from a collection of cells, are those wherein the condition caused to exist in beads containing either a desired or undesired cell affects the weight or density of the bead. In this manner, the isolation of beads containing desired cells from beads containing undesired cells can be achieved expeditiously.

Figure 10A:
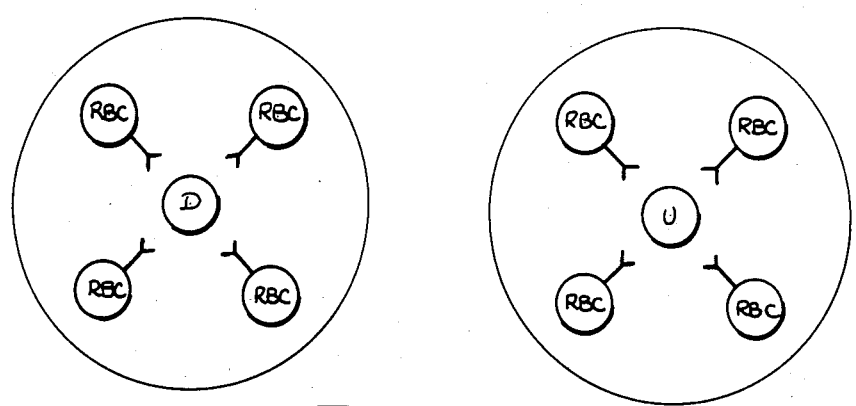
FIGS. 10A through 10C; 11A through 11D; and 12A through 12E, illustrate schematically methods for isolating cells producing a desired product.
Figure 10B:
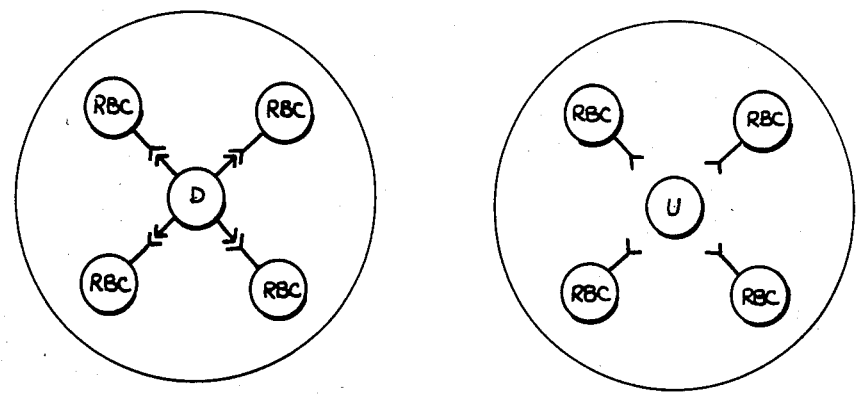
Figure 10C:
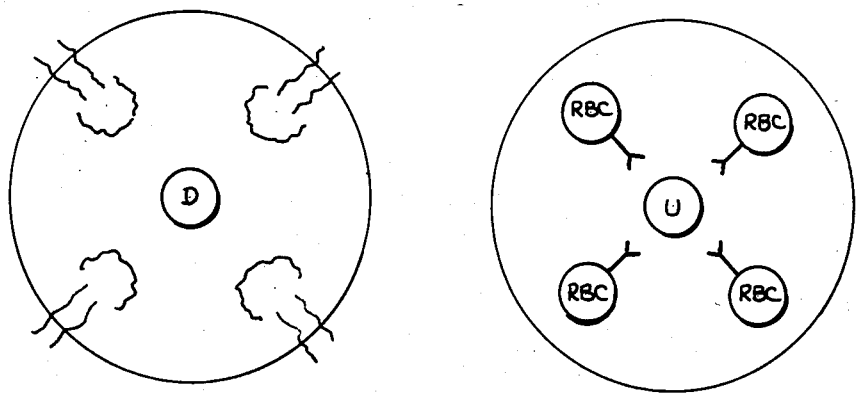

By way of example, and with reference to FIGS. 10A through 10C, the individual cells of a mixed cell population (containing both desired and undesired cells, wherein the desired cells are those making a particular antibody) are encapsulated within semi-permeable material to form beads. Within each bead, it is arranged that a large number of red blood cells are present, each red blood cell having affixed to its surface the antigen specific to the desired antibody (see FIG. 10A, where antigen is represented by—<). All the beads are suspended in a medium suitable for cell growth.

After a sufficient amount of time has elapsed for cells to produce and release products, the condition which exists is represented by FIG. 10B. In only those beads containing desired cells will there occur an interaction between the antigenic receptor on the red blood cell and the product, produced by the cell, which is specific to that antigen. In all other cases, i.e., where no products are made or product other than the desired product are made, no binding to the antigen on the red blood cell will occur.

Upon addition to the entire population of complement (as to which the bead material is permeable), there will occur lysis of those red blood cells having antigen/antibody complexes thereon. Thus, the only red blood cells lysed by the complement addition will be those contained within those beads containing a desired cell, for only in such beads will the antigen on the red blood cell have complexed with antibody. Red blood cells in all other beads will remain intact.

The permeability of the encapsulating bead material is chosen such that the lysed red blood cell components can permeate through the material to the surrounding medium (FIG. 10C). As a result of the loss of the lysate, those beads containing a desired cell are now significantly lighter (less dense) than all other beads and will then be capable of separation therefrom via gravimetric techniques.

The foregoing method is highly suitable in all those instances where antigen specific to the desired antibody can be affixed to a red blood cell. However, in many instances it may not be possible to affix the antigen to a red blood cell, either because the removal of antigen from a nucleated cell on whose surface it is present, or the means for affixing the antigen to the red blood cell, is difficult and/or destroys or alters the antigenic nature or specificity of the desired antigen. In such cases, the source of such antigen necessarily must be the nucleated cell on whose surface it is present. However, unlike red blood cells, it is extremely difficult to bring about the lysis of nucleated cells by any means; hence, an isolation method directly comparable to that described above for red blood cells (e.g., FIGS. 10A through 10C) cannot be employed.

To deal with these situations, i.e., where the antigen specific to the desired antibody is carried on a nucleated cell which cannot easily be lysed, the following methods have been developed.

In one method, illustrated by FIGS. 11A through 11D, each cell of the mixed cell population is encapsulated in a semipermeable material to form beads. Within each bead, it is arranged that, e.g., a tumor cell(s) ("T" in FIG. 11A), bearing the antigen specific to the desired antibody sought, be present. All the beads are suspended in an appropriate growth medium.

Figure 11A:
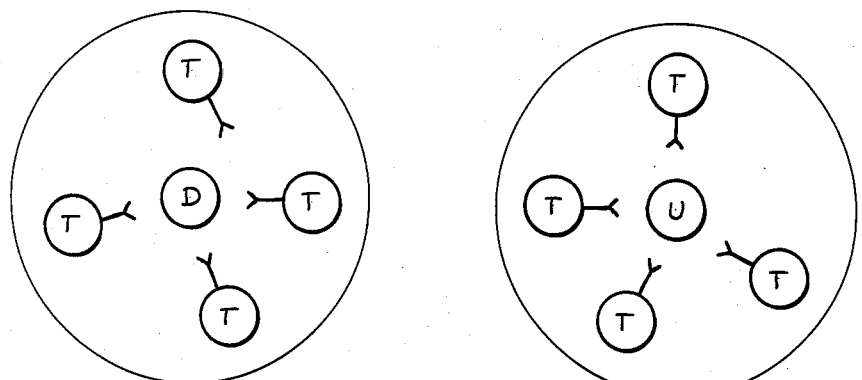
Figure 11B:
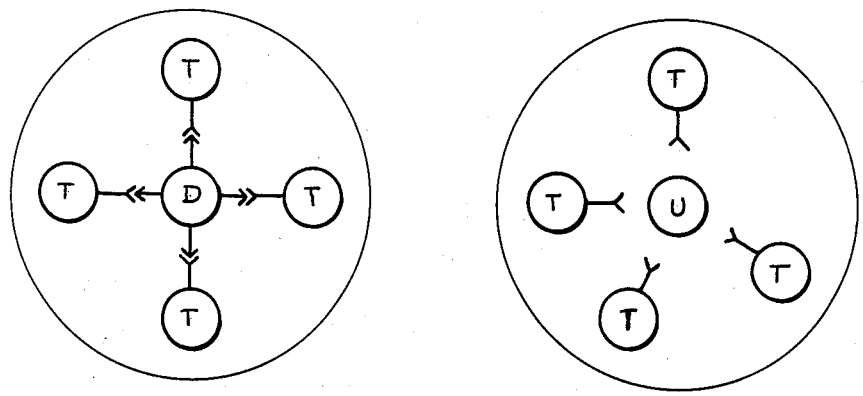
Figure 11C:
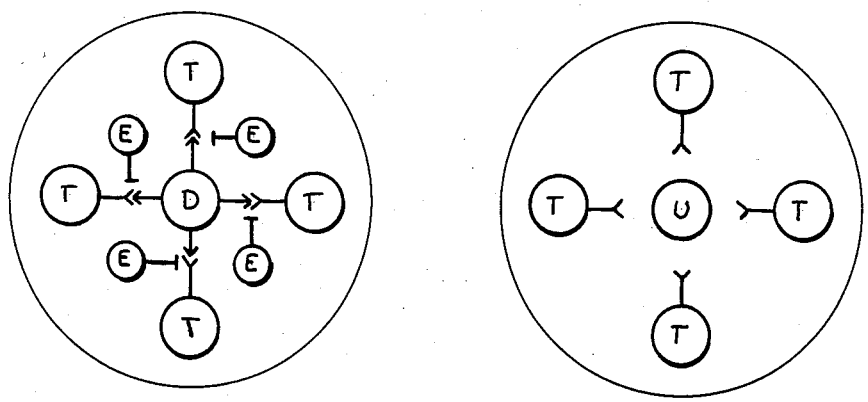

After a suitable incubation period, those beads containing desired cells will contain desired antibody product which specifically binds to the antigen on the tumor cell. No such interactions will occur in beads containing cells not making desired antibody (see FIG. 11B). Thereafter, there is added to the entire cell population, a complex of an anti-immunoglobulin (anti-product$_2$) and an enzyme. The complex is permeable through the bead material, but becomes affixed only in those beads where antigen and antibody have complexed, i.e., only in those beads containing desired cells (FIG. 11C).

Figure 11D:
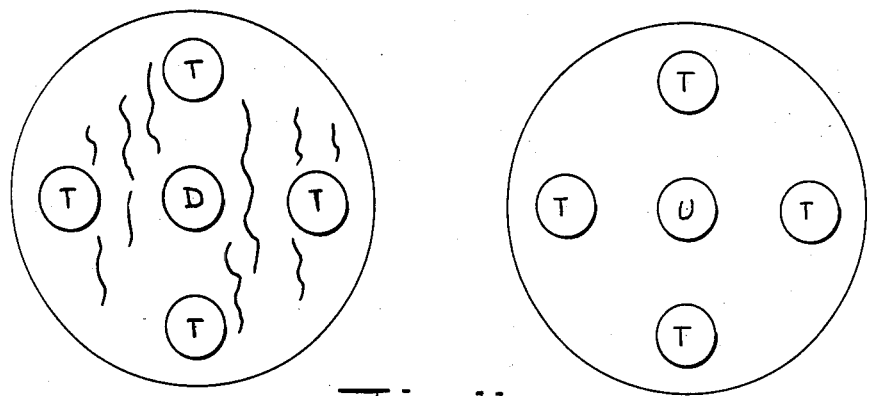

After washing away any unbound anti-Ig/enzyme complex, there is next added to the entire cell population a soluble material which, through the action of the enzyme carried by the anti-Ig, is converted to an insoluble precipitate. Thus, since enzyme is present only in those beads containing desired cells, an insoluble precipitate will be formed only in the beads containing desired cells (FIG. 11D). This causes the beads containing desired cells to be much heavier (more dense) than beads containing undesired cells, and separation can be accomplished by simple gravimetric methods.

The foregoing method can be modified to give an "amplified" response, i.e., wherein the beads containing the desired cells can be made even heavier than can be accomplished simply by means of the enzyme-induced conversion and precipitation of insoluble material. This amplification comes about by adding to the entire system a material which will bind to the precipitate which has formed in the beads containing desired cells. This material (in the nature of an antibody to the precipitate) can be chosen to be large (provided it can permeate the bead material) and, since it will affix only where precipitate exists (i.e., only in beads containing desired cells), the weight of such beads is greatly increased over those beads where no precipitate (and, hence, no "antibody" thereto) exists, i.e., beads containing undesired cells. In this manner, gravimetric separation is even more easily achieved.

The foregoing amplification technique can also be applied in the earlier-described method (FIGS. 10A through 10C) wherein red blood cells, carrying antigen specific to the desired antibody, are lysed. In this case, the semi-permeable bead material is chosen so as to retain certain components of the lysed red blood cells, in particular, the haemoglobin. Since lysis occurs only in those beads containing desired cells, free haemoglobin will exist only in those beads containing desired cells. After lysis has occurred, an antibody to haemoglobin can be added to the system in large quantities and will bind to and become immobilized only where free haemoglobin exists. In this manner, beads containing desired cells can be made to be much heavier than beads containing undesired cells, and gravimetric separation is, therefore, facilitated.

Another method for isolating cells where the antigen specific to the desired product must be carried on a cell which cannot per se by lysed is as follows. Referring to FIGS. 12A through 12E, the individual cells of the cell population are encapsulated within semi-permeable material to form beads. The beads are arranged (see FIG. 12A) to include, in addition to the cell, tumor cells em-carrying the antigen (—<) specific to the desired antibody and red blood cells carrying a product (—) thereon (described in more detail hereinafter).

Figure 12A:
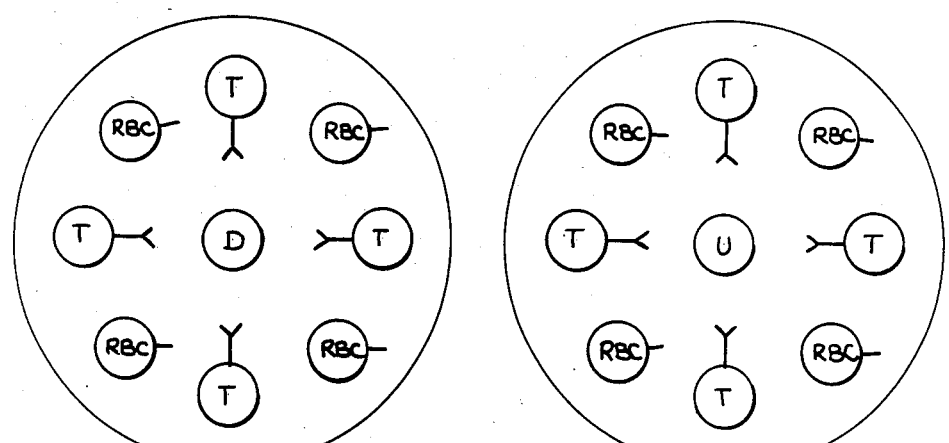
Figure 12B:
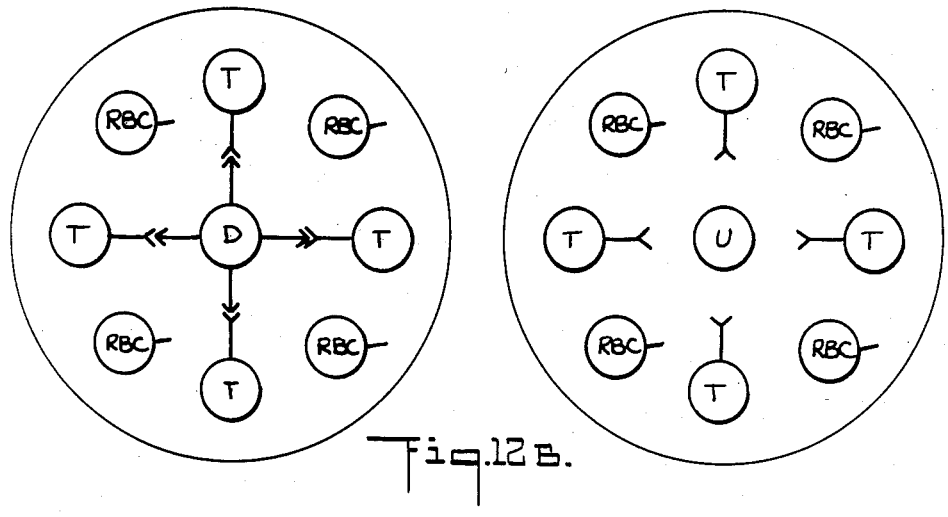
Figure 12C:
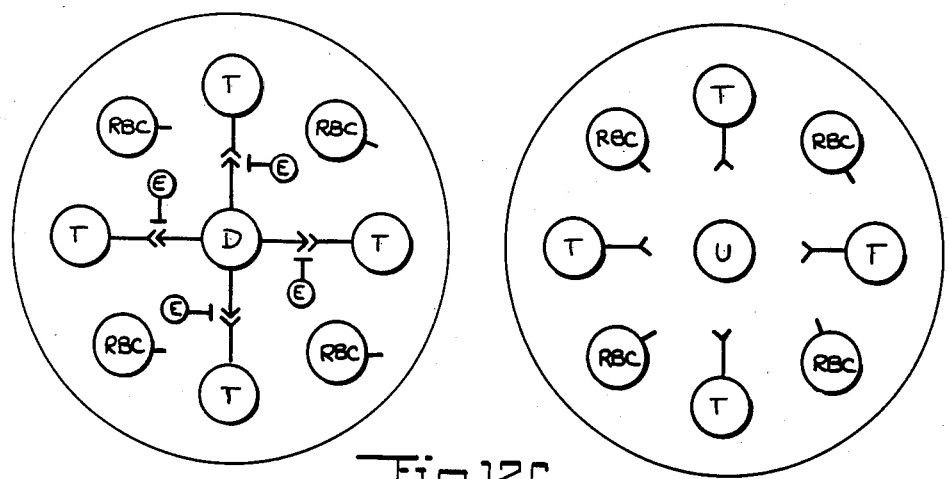

After a suitable incubation period, desired antibody product being made and released by a desired cell becomes affixed to the specific antigen (FIG. 12B). Thereafter, a suitable anti-product$_2$ (e.g., anti-immunoglobulin) to which an enzyme is complexed is added to the entire population. This complex becomes affixed only in those beads where an antibody/antigen interaction has occurred, i.e., only in those beads containing desired cells (FIG. 12C). Hence, after washing away unbound anti-Ig/enzyme complexes, the only beads containing enzyme are those beads containing desired cells.

Figure 12D:
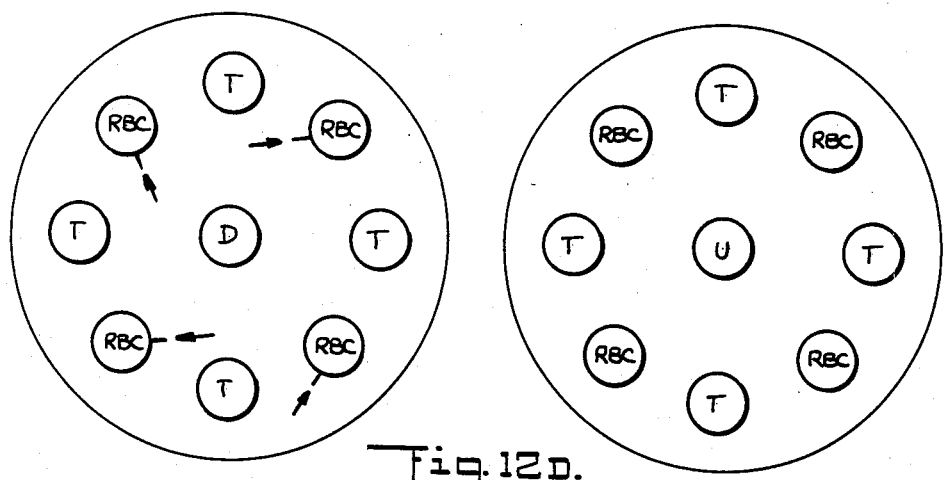
Figure 12E:
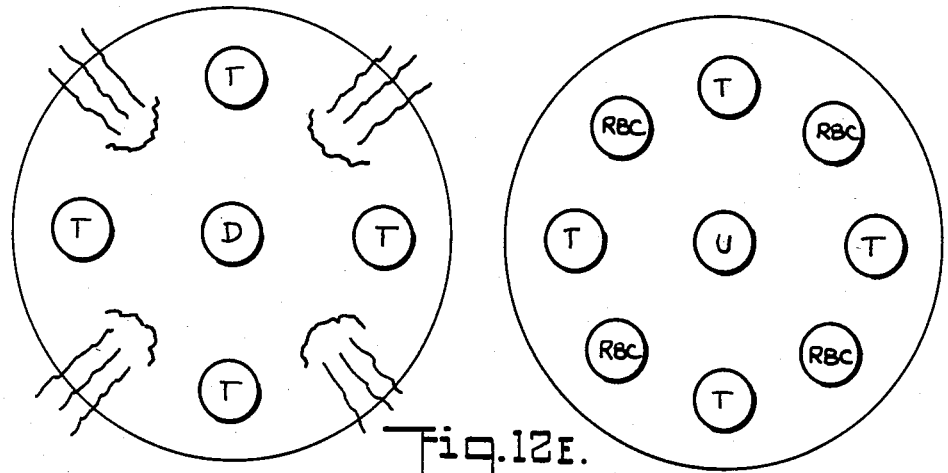

The enzyme affixed in the beads containing desired cells is chosen to be one capable of enzymatically converting a particular compound (added to the entire cell population) into a compound (→ in FIG. 12D) which shows antigenic specificity for the compound (—) pre-affixed on the surface of the red blood cell. In this manner, there is caused to occur, only in the beads containing desired cells, an antibody/antigen interaction on the surface of the red blood cells (FIG. 12D). Once this condition exists, it is possible to add, e.g., complement to the system and cause lysis of the red blood cells only in the beads containing desired cells. The contents of the lysed red blood cells permeates out through the bead layer (FIG. 12E) and, as a result, beads containing desired cells will be lighter (less dense) than beads containing undesired cells (the latter beads still possessing intact red blood cells), thereby permitting gravimetric separation of beads.

In any of the foregoing embodiments where tumor cells are employed within the beads as a "carrier" for a particular antigen, it will be appreciated that these tumor cells will undergo growth and subdivision during the time period in which the various interactions and reagent/compound additions are taking place. Since the isolation methods described above rely upon ultimate relative weight differences between beads containing desired cells and beads containing undesired cells, it is possible that errors could occur if, as often may be the case, the growth rate of the tumor cells employed in each bead is not uniformly consistent. Thus, for example, where the isolation depends upon the formation of an insoluble precipitate in beads containing desired cells (see FIGS. 11A through 11D), thereby making them heavier than beads containing undesired cells, it is possible that in one or more beads containing undesired cells the antigen-bearing tumor cells therein divide and subdivide at a rate faster than occurs for tumor cells in one or more of the beads containing desired cells. If the rate of tumor cell sub-division in such beads (containing undesired cells) is sufficiently large, the bead may become as heavy as one containing a desired cell, even though the former has no insoluble precipitate formed therein. As such, it may incorrectly be taken to be a bead containing a desired cell.

Generally, two methods are available to avoid the possibility of this occurring. On the one hand, the various interactions which cause beads having desired cells to contain (or not contain) a material not present (or present) in the beads having undesired cells can be arranged (e.g., via the earlier-described amplification techniques) to be so numerous as to result in weight differences very much larger than any weight differences which could occur as a result of differing rates of tumor cell growth. Alternatively, the tumor cells employed as antigen carriers can, before being mixed with other cells and encapsulated within beads, be irradiated so as to cause their death to occur at some point in the process after their function (providing antigen to capture antibody being made by a desired cell) has been completed. Another alternative is to cool the beads which will greatly slow the matabolism and growth of the cells and therefore the weight of the bead will not change as a result of cell growth.

In all of the foregoing methods, the desired cells per se can be "protected" from the action of any of the agents, etc. employed to accomplish bead differentiation (either by color, weight, fluorescence, etc.). Thus, for example, the individual cells of the cell population can first be encapsulated within semi-permeable material to form beads. These beads are themselves then encapsulated within another semi-permeable material and it is in this "outer layer" where materials such as red blood cells, tumor cells, etc. are contained. The semi-permeable material used to encapsulate the cells per se is chosen so as to permit product produced by the cells to migrate therethrough into the outer layer for interaction with whatever agents (e.g., antigen-carrying red blood cells or tumor cells) are there present, but to resist passage (into the inner bead) of the various reagents used in the process. In this manner, the means by which beads containing desired cells and beads containing undesired cells are differentiated occurs in the outer layer. Once isolation of beads containing desired cells is achieved, the outer layer can be removed, leaving only the beaded, desired cells. The desired cells can then be recovered from their beads without any interference or contamination from the various materials which were used in effecting the differentiation.

Another important feature of cell isolation techniques which depend upon weight (density) differentials to effect separation of beads is the weight and density uniformity of the beads at the commencement of the process. As described in more detail hereinafter, the mechanism of bead formation is such that, statistically, a single cell from the cell population and, where applicable, one or more other cells (red blood cells, tumor cells) or carriers are contained within each bead. However, it may turn out that certain beads contain more or less cells than other beads and, moreover, may differ in overall size, weight and density. When this full distribution of beads is employed in one of the earlier-described weight or density-dependent isolation techniques, the weight or density differentials caused to occur (e.g., via lysis or precipitate formation) between beads containing desired cells and beads containing undesired cells may be on the same order of magnitude as some of the weight or density differentials inherent in the beginning beads per se. As such, a number of beads may be incorrectly isolated simply because they were heavier or lighter than other beads to begin with.

This possible difficulty can be overcome by arranging that the intentionally caused weight or density differentials are very much larger than any inherent differentials in the beginning beads, i.e., through use of the earlier-described amplification techniques. A more preferred solution, however, is to subject the formed beads, prior to use in an isolation technique, to a means whereby beads of closely similar weight and density aggregate. Thus, for example, all the beads can be added to a vertical column containing a fluid of specified viscosity and density such that beads of the same or closely similar weight and density will collect together at various levels in the fluid. For use in an isolation technique, only beads from the same fluid level are employed, thereby insuring that weight and density differentials noted in the isolation process are the result of intentionally caused conditions rather than inherent dissimilarities in the starting bead population.

As earlier mentioned, a number of techniques are available for forming beads containing individual cells of the cell population and any other materials (e.g., antigen-bearing red blood cells or tumor cells, carriers, etc.). Generally, the techiques involve formation of a suspension of the cell population (and other materials) in an appropriate gel-forming medium such as alginate or agarose. The suspension is constantly stirred to insure homogeneity and, e.g., a needle-like device is employed to draw off very small quantities thereof and deposit them as droplets into a medium which causes the droplets to form coherent beads. Thus, for example, where alginate is the gel-forming medium, the droplets may be deposited in a calcium ion-containing solution (e.g., $CaCl_2$) to cause gellation of the alginate. Where agarose is the gel-forming medium, the droplets may be deposited in an oil solution maintained at a temperature sufficiently low to cause the agarose to gel. A mixture of alginate and agarose may also be employed as the gel-forming medium, in which case the droplets are deposited into a calcium-containing solution maintained at low temperature.

It is also possible to employ droplet forming and depositing devices which are fed, from separate metered inlet sources, with cells (and other materials) and the gel-forming medium, after which a droplet of the now mixed cells and medium is deposited into a solution (e.g., calcium-containing or cold oil) which causes gellation. Beads may also be formed by emulsifying cells and gel-forming medium to form small, discrete droplets containing cells and the gel medium, after which the droplets are subjected to conditions which cause their gellation into discrete spherical beads.

Other means for forming beads containing individual cells of the cell population include means whereby a preferred cylinder is used to contain a suspension of cells and gel-forming medium. The cylinder is itself placed in a medium appropriate for gelling whatever gel-forming material is employed, and is rotated therein so as to spin-off, through the perforations, small discrete droplets of gel-forming medium and cells. These droplets immediately encounter the medium which causes gellation of the gel-forming material (e.g., cold oil, calcium-containing solution) and results in the formation of coherent beads.

In each of the bead-forming mechanisms, the concentration of cells, the concentration of gel-forming medium and the size of the droplets formed are chosen such that each droplet (and, hence, each bead ultimately formed therefrom) contains one cell of the cell population and, where appropriate, a specified number of other materials such as antigen-bearing red blood cells, tumor cells, etc.

The gelled beads or microspheres formed according to any of the foregoing techniques may be used per se as the beads in the various cell isolation methods previously described. Generally, however, it is preferred to surround each gelled microsphere with a semi-permeable material and then dissolve the gelled material of the microsphere so as to form a bead, containing the components present in the gelled microsphere, but now constituted of the semi-permeable material as the bead material. Thus, for example, alginate microspheres can be surrounded by a layer of polylysine (via electrostatic attraction) and the thus-formed beads subjected to a medium which removes calcium ions from the microspheres (e.g., a solution of calcium sequestering agent or a calcium-free solution). This causes the microspheres to liquify and the result is a bead consisting of polylysine encapsulating the cell and other components present in the originally formed microsphere. The same technique can be employed where the gelled microspheres were formed from agarose or an agarose-alginate mixture, wherein the agarose microspheres, surrounded by a semi-permeable material such as polylysine, is subjected to, e.g., hot oil or other fluid so as to dissolve the agarose gel and result in a polylysine bead. Since polylysine has little or an electrostatic attraction toward agarose, it may be desirable to utilize a small amount of alginate in forming the predominantly agarose microspheres, sufficient to cause the polylysine to be electrostatically attracted to, and surround, the microsphere; the alginate portion of the microsphere in the resultant bead can then be dissolved as earlier described.

In those instances where a second or outer bead layer is employed, i.e., where the various bead differentiation agents (and ultimate differentiation reactions) are to be confined to an outer layer separate from the cell-containing bead, the various bead-forming techniques can be used to surround the cell-containing beads with outer beads of, e.g., alginate, agarose, polylysine, etc.

The various "isolation" procedures of the present invention possess far-ranging applicability with respect to the finding and isolation of any desired cell in a population or grouping of cells containing these desired cells in admixture with so-called undesired cells. To recapitulate much of what has been described in considerable detail earlier in this application, the techniques herein are useful where it is desired to find, for example, and cells in a cell population making a particular product (e.g., insulin or particular antibody). In this case, the undesired cells simply are those not making the desired product. At the same time, however, this gross isolation of desired from undesired cells also inherently locates and isolates those "desired" cells making the largest quantity of desired product (i.e., making desired product at the fastest rate). Location and isolation of these high production cells is highly desirable since such cells, when cultured, will produce the largest quantity of desired product per unit cost, thereby permitting the overall ultimate process (i.e., the production of, e.g., antibodies, insulin, etc.) to be greatly optimized.

By way of further explanation, use of the isolation technique of, says, FIGS 11A through 11D to locate and isolate cells making, for example, an antibody to a particular antigen, relies upon selectively increasing the weight and density of those beads containing such desired cells as compared to all other beads in the population. The weight increase is brought about by the enzymatic conversion, in the bead containing a desired cell, of an added soluble compound to an insoluble precipitate. This conversion is confined to beads containing desired cells by virtue of the fact that the required enzyme is present only in such beads. The enzyme is present only in such beads by virtue of the fact that the carrier for the enzyme, e.g., anti-immunoglobulin, will become affixed only in beads containing desired cells because only in such beads will there exist antibody/antigen complexes for binding of the anti-immunoglobulin. The antibody/antigen complexes exist only in beads containing desired cells because, by definition, only in such beads is antibody specific to the antigen (carried on a nucleated cell) being produced. As is apparent, therefore, the absolute amount of enzyme present in a bead containing a desired cell is directly proportional to the amount of desired antibody being produced by that cell (the amount of enzyme is proportional to the amount of anti-Ig which can be affixed in the bead, and this in turn is proportional to the number of antibody/antigen complexes in the bead, which is proportional to the absolute amount of antibody produced by the cell in the beads).

In this method, therefore, all beads containing desired cells (i.e., cells making the particular antibody sought) will be made heavier than all other beads in the population and, thus, will be isolated from all other beads by virtue of their ability, in a suitable liquid medium and under the influence of gravity, to sink to a level below that occupied by all other beads. Among these heavier beads containing desired cells, however, will be beads which sink either faster and/or to a lower level in the medium as compared to other beads containing desired cells, because more of the insoluble precipitate has formed therein. Since the amount of precipitate formation is directly proportional to the amount of antibody produced by the cell in the bead, these beads necessarily contain those desired cells in the population making the largest amount of antibody at the highest rate. Still further optimization can be achieved by selecting from this first isolation just those desired beads which, based on their rate of descent in the medium and/or the level to which they descend, contain desired cells making, relative to all desired cells, the most antibody at the fastest rate. These cells can then be cultured and subjected to a repeat of the isolation procedure in order to make a further selection, in the same manner, of the very highest producing cells from among all these high production cells. The culturing/isolation can be repeated as many times as desired in order to find cells making the largest amount of product per given unit of time. These cells are then used as a source for making and collecting desired antibodies (i.e., in an appropriate culture medium). Because of the high antibody production rate of the cells employed, the process is economically optimum, i.e., the amount of antibody obtainable for a given quantity of culture medium, size of culture chamber, etc. is maximized.

The isolation methods of the present invention, therefore, are capable of locating and isolating cells in a cell population producing the greatest number of desired product molecules per cell per unit time. The reason why certain cells in a cell population make more desired product per unit time than do other cells in the cell population (also making desired product) is not per se important, just so long as such cells can be located and isolated. For example, the increased rate of desired product production by a particular cell could be because of the inherent genetic make-up of the cell; or because the genetic mechanism of the cell has been intentionally altered; or because the cell is one which has undergone spontaneous gene amplification, i.e., where it is a descendant of the cell which, upon division and sub-division, produces cells having up to twice as many genes (coded for production of a particular product) as the previous cell.

The foregoing discussion is equally applicable to isolation methods wherein desired cells are distinguished from undesired cells by means of the lighter weight of beads containing them, their ability to be rescued from a noxious environment, etc. For example, one of the earlier-described isolation techniques involves the ability of desired cells in a cell population to be selectively rescued from or selectively protected from a methotrexate environment otherwise lethal to the cells. In this technique, individual cells of the cell population are encapsulated in beads along with nucleated cells (or other carrier material) bearing thereon an anti-product (e.g., antigen) specific to the desired product (e.g., antibody) being made by desired cells. The beads are suspended in a medium which includes methotrexate and dihydrofolic acid. The methotrexate irreversibly binds the folic acid reductase of the cells and therefore prevents the cells from converting the dihydrofolic acid to the folinic acid needed for life. There is then added to the system an anti-product$_2$ (e.g., anti-immunoglobulin) to which is coupled folic acid reductase of the special mammalian cell variety, which is resistant to the effects of methotrexate). The anti-Ig (and hence the enzyme) becomes affixed only in those beads where an antibody-antigen interaction has occurred, i.e., only in those cells making the desired antibody product. The presence of the enzyme in these beads permits the conversion of the dihydrofolic acid to folinic acid and thereby permits the cells in these beads to survive the methotrexate environment, notwithstanding the fact that the folic acid reductase of the cells per se has been inactivated. In this manner, the beads containing desired cells will be the only beads in the population containing living material, and can thus be isolated from all other beads.

As in the previous embodiment, involving precipitate formation in desired beads, the amount of methotrexate resistant folic acid reductase caused to be present in beads containing desired cells is directly proportional to the amount of desired product (antibody in this case) being made by the desired cells. Hence, the degree of conversion in any bead of dihydrofolic acid to folinic acid, brought about by the methotrexate-resistant enzyme, also is directly proportional to the amount of desired antibody being made by the cell within the bead. Because of this, it is possible to isolate desired cells making the largest amount of antibody per unit time simply by repeating the isolation procedure one or more times using increasing doses of methotrexate. Cells that survive (and are isolated) at each succeeding dose are those cells making the highest amount of antibody per unit time, since in the beads in which such cells are encapsulated, the high antibody production results in the presence therein of more resistant folic acid reductase (which in turn converts more dihydrofolic acid to folinic acid and thus permits the cells to survive in a particular concentration of methotrexate). These highest production cells, which are high antibody producers because of their inherent genetic makeup or because they are cells resulting from spontaneous gene amplification or for any other reason, are those which will then be used to produce antibodies in the most economical manner.

Within the context of the isolation of "desired" cells from "undesired" cells according to the present invention, many practical, and simple, processes can be performed. By way of example, if the desired product being produced by the desired cell is a product required by some other cell or organism for life, all that is required is to encapsulate the individual cells of the population along with one or more of the cells which require the desired product in order to live. If the desired product is being produced by the cell in a particular bead, the cells which require that product for life will grow within that bead. In all other beads, the cells which require the product for life will die. Hence, beads containing desired cells, making desired product, will, with time, become heavier or denser than all other beads in the population due to the growth of cells therein. An example of this method is the location of desired cells making T cell growth factor, required for life by T cells. The individual cells of the population are encapsulated in beads along with T cells. If a bead contains a cell making the desired T cell growth factor, the T cells therein will grow.

Another example along the same lines is the isolation of organisms making a desired product such as an antibiotic. The individual organisms of the population are encapsulated in beads along with some organism ("responding organism") whose growth is inhibited by the particular antibiotic. If an organism from the population is making the antibiotic, growth of the responding organism in the bead in which the antibiotic is being made will be inhibited, while in all other beads the responding organism will fluorish. Beads containing the desired organism, i.e., the organism making the desired antibody, will therefore be lighter than all other beads.

Another practical use of the general technique of this invention is the isolation of cells not making a particular product. For example, in the use of hybridization procedures to produce hybrid cells making monoclonal products, it is necessary that the immortal cell parent of the hybrid (e.g., a myeloma cell) not itself produce antibody products, since otherwise the production of these antibodies will be carried through to the hybrid cell and the hybrid cell will, therefore, produce a mixture of antibodies rather than monoclonal antibody. The present invention provides a simple means for finding, e.g., myeloma cells (for use in hybridization) which make no antibody products themselves. Thus, the individual myeloma cells of a myeloma cell population are encapsulated in beads along with suitably immobilized anti-immunoglobulin or Staph. (antigen specificity to any particular antibody being made by the myeloma is not required since myeloma cells making specific antibody products are not being sought; the production of any antibody by the myeloma cell is what is sought to be detected). The bead population may then be sujbected to any of the various lysis, or enzymatic-dependent, etc. techniques previously described to isolate all beads containing cells making any antibody products. In those beads where no reaction occurs are present the desired myeloma cells, i.e., myeloma cells not themselves producing antibodies.

Yet another practical application of the isolation processes of this invention is the monitoring of culturing cells so as to ascertain whether they are producing product (either at all or at some acceptable rate). Thus, in a method wherein cells producing particular products (e.g., antibodies) are cultured in a suitable medium and the antibodies produced by the cells continuously or periodically collected for ultimate use, the economics of the method (i.e., the cost of producing a unit amount of antibody per unit cost of the culturing method, apparatus, etc.) are obviously more attractive if (as earlier discussed) the cells being cultured produce a large quantity of product per unit time. The culturing process for mass producing antibodies, etc. becomes less economically optimal where the cells being cultured produce either only small amounts of antibody or, with time, stop producing antibody altogether. Accordingly, even though the culturing process begins with use of high production cells, and hence is economical at its inception, it would be desirable to provide a method for periodically testing the cells to see if they continue to be high producers of antibody (or, indeed, to see if they might have stopped producing product altogether). In this manner, undesired low production (or "no production") cells can be removed from the culture system, permitting savings in culture medium, product removal mechanisms, etc.

With the processes of this invention, the foregoing can be accomplished simply by periodic (or continuous) removal of a quantity of cells from the culture medium followed by encapsulation of each individual cell so removed in a bead along with the other materials or cells required for any of the previously-described isolation techniques, e.g., antigen or anti-product carried on a suitable support (e.g., red blood cells, nucleated cells) or as part of the bead material itself. Generally, the cells being cultured are hybrid cells making a monoclonal product (antibody); accordingly, the anti-product need not be specific to the product produced by the cell but can, instead, be simply anti-immunoglobulin or Staph. since, by definition, only one type product is being produced by the hybrid cells.

The beads are then subjected to any of the previously described isolation techniques in order to isolate therefrom only those beads containing cells making the highest amount of product (desired product) per unit time. All other beads can be discarded and, after dissolution of the bead material, these desired high production cells can be returned to the culture system for continued production and removal of product.

The isolation techniques of the present invention can be practiced in either a batch, continuous or semi-continuous mode for all or individual steps in the process. Continuous processing is, of course, preferred from an economic point of view. One means for continuously isolating desired cells from undesired cells is illustrated in FIG. 13 for an isolation procedure based upon the selective death of undesired cells.

In FIG. 13 there is shown, in greatly exaggerated dimension, a long hollow fiber 14 made of semi-permeable material. The fiber is divided on its outer perimeter into sections (I, II, III and IV) by cylindrical housings 18 spaced along the length of fiber 14. A mixture of a cell population (in which some of the cells are making a desired product), an oil/water medium and an anti-product to the desired product (e.g., where the desired product is antibody, antigen specific thereto) is formed in stirred vessel 10 and is then fed to a series of needles 12. Oil and water spheres 16, containing a cell from the cell population and antigen specific to the desired antibody are expelled from needles 12 into hollow fiber 14.

In hollow fiber 14, the cell-containing spheres are subjected to a particular dose of methotrexate, which inactivates the folic acid reductase of all the cells per se, and prevents the cells from converting dihydrofolic acid to folinic acid. By the time the cells reach the end of hollow fiber 14, they will be dead by virtue of the lack of folinic acid unless they are rescued from this condition.

The rescue of cells is confined only to desired cells in the following manner.

In a first section (I) of hollow fiber 14, the cell-containing spheres or droplets are contacted with a complex of anti-immunoglobulin and methotrexate-resistant folica acid reductase added through the permeable fiber surface. The anti-Ig/enzyme complex will remain affixed only to those spheres where the antigen present therein has interacted with its specific (the desired) antibody, i.e., only in those spheres containing a desired cell. Excess, unbound anti-Ig/enzyme complex will exit the hollow fiber both at section I and in section II, where the spheres are suitably washed.

In the next section (III) along hollow fiber 14, dihydrofolic acid is added through the permeable fiber surface. The dihydrofolic acid will be converted to folinic acid only in those spheres where methotrexate resistant folic acid reductase exists, i.e., only in those spheres containing a cell making desired product. As a result, these desired cells will live while all remaining cells, lacking folinic acid, will die.

In the next section (IV) of hollow fiber 14, materials which may be required to maintain the living desired cells can be added, e.g., culture medium, oxygen-bearing gases, etc.

All the cell-containing spheres thereafter travel through tube 22 (which could simply be an extension of hollow fiber 14) to an area where spheres containing living (desired) cels can be separated from spheres containing non-living cells. The latter are discarded through line 20 while the former continue their passage through tube 22 to a means for breaking the spheres to liberate the living cells per se.

Where it is desired to isolate those cells making the highest amount of antibody, the living cells isolated in this first pass through hollow fiber 14 can simply be recycled to stirred container 10 for re-formation into spheres (with antigen) and again sent through hollow fiber 14, but this time under the influence of an increased dose of methotrexate. The living cells recovered from this pass through hollow fiber 14 can be continuously recycled through the process in this manner, under increasing doses of methotrexate, so that the ultimate living cells isolated are those making the highest quantity of desired antibody per unit time.

In the method and apparatus illustrated in FIG. 13, the hollow fiber 14 can be manufactured so as to have varying permeability as between one or more of the sections I through IV so as to insure that, in certain sections, various materials can be freely added while, in other sections, materials within the fiber (e.g., folic acid produced in III) cannot escape.

In the present invention, desired cells—be they cells producing and releasing a particular product or cells characterized by having a particular product on or as part of their surface—are isolated from other, undesired cells by methods which are based upon the ability of the product to either directly or indirectly bring about a condition (or absence of a condition) only in the vicinity of the desired cells, which condition can be used to distinguish desired cells from undesired cells. As is apparent from the foregoing description, a number of such methods can be used to bring about this result. The methods described, as well as particular materials and conditions employed in these methods, are intended to illustrate rather than to limit the invention and, indeed, various modifications and the like will be apparent to and ascertainable by those skilled in the art without departing from the scope, spirit and essential features of the present invention. Simply by way of example, a number of the isolation techniques described herein utilize as a critical step the capture and immobilization of the desired product (being produced by a desired cell) by a material (anti-product) exhibiting specific affinity therefor. This anti-product may be antigenic where the desired product is an antibody, or an antibody where the desired product is antigenic. In addition, the anti-product may be one which exhibits electrostatic affinity for the product or a synthesized chemical which exhibits specific binding affinity for the product.

It also is possible to genetically alter the desired cell per se so as to produce the desired product in a form modified in a way which facilitates the desired product's capture by anti-product. Thus, for example, a cell population from which it is desired to isolate cells making, e.g., insulin, can be subjected to any of the described isolation methods, using where necessary an antibody to insulin as the capturing anti-product, to locate desired cells making insulin. If it is desired to then isolate from all recovered cells making insulin just those cells making the largest quantity of insulin per unit time, the isolation process may, as described earlier, be repeated one or more times on the population of insulin-producing cells. In these repeat isolations, insulin capture by anti-product can be facilitated by appending to the genes of such cells responsible for insulin production a gene coded for production of, e.g., polylysine. Insulin molecules thereafter produced by these cells will contain polylysine and therefore can be captured by materials exhibiting electrostatic attraction to the highly positively-charged polylysine component of the insulin. This same technique can be employed to locate cells which undergo gene amplification, since amplification of the insulin gene will also amplify the appended polylysine gene and insulin product produced by such cells will have a correspondingly large quantity of polylysine thereon.

What is claimed is:

1. A method for isolating desired cells, which make and secrete a particular product, from a population of cells containing the desired cells in admixture with undesired cells which either do not make and secrete the particular product or which make and secrete the particular product at a rate per unit time which is lower than that of desired cells, comprising the steps of:
   (a) affixing to the surface of red blood cells a ligand which exhibits specific affinity for the particular product;
   (b) encapuslating the cells of said cell population and red blood cells of step (a) within discrete beads made of a material which (1) will retain cells within the bead structure while permitting the cells to be nourished within the bead by nutrient medium, (2) retain the red blood cells of step (a) within the bead, (3) permit introduction into the bead of agents comprising complement which are capable of bringing about lysis of red blood cells and (4) permit egress from the beads of the hemoglobin of red blood cells lysed via complement-mediated lysis, the encapsulation being performed under conditions which substantially result in the presence in each bead of no more than one individual cell from the population and a plurality of red blood cells of step (a);

(c) suspending said beads in a nutrient medium capable of supporting growth of cells of said population within said beads;

(d) permitting sufficient time to elapse for particular product to be made and secreted by desired cells and for such particular product to bind to the ligand therefor carried on the surface of the red blood cells within those beads containing a desired cell;

(e) incubating the beads with agents comprising complement under conditions which bring about complement-mediated lysis within beads of red blood cells which carry on their surface a complex of ligand and desired product, such lysis resulting in escape from those beads of the hemoglobin of the lysed red blood cells therein, thereby reducing the density of such beads relative to other beads;

(f) suspending said beads in a gradient medium which permits beads of distinguishable density difference to aggregate at distinguishable vertical levels in the gradient medium; and (g) separating from said gradient medium those beads which aggregate at the uppermost vertical level in said gradient medium.

2. The method according to claim 1 wherein said particular product is an antibody, and said ligand is an antigen exhibiting specific binding affinity for said antibody.

3. The method according to claim 2 wherein said encapsulating material comprises agarose.

4. A method for isolating desired cells, which make and secrete a particular product, from a population of cells containing the desired cells in admixture with undesired cells which either do not make and secrete the particular product or which make and secrete the particular product at a rate per unit time which is lower than that of desired cells, comprising the steps of:

(a) encapsulating the cells of said cell population together with carrier materials bearing on their surface a ligand exhibiting specific affinity for said particular product and together with red blood cells bearing on their surface a ligand exhibiting specific affinity for a specific conversion ligand, said encapsulation being within discrete beads made of a material which (1) will retain cells within the bead structure while permitting the cells to be nourished within the bead by nutrient medium, (2) retain the carrier material and red blood cells within the bead, (3) permit introduction into the bead of an enzyme-bearing ligand and a substrate for the enzyme, (4) permit introduction into the bead of agents comprising complement which are capable of bringing about lysis of red blood cells (5) permit egress from the beads of the hemoglobin of red blood cells lysed via complement-mediated lysis, the encapsulation being performed under conditions which substantially result in the presence in each bead of no more than one individual cell from the population, a plurality of said carrier materials and a plurality of said red blood cells;

(b) suspending said beads in a nutrient medium capable of supporting growth of cells in said population within said beads;

(c) permitting sufficient time to elapse for particular product made by a desired cell to become affixed to the ligand therefor provided on the surface of carrier materials within those beads containing a desired cell;

(d) incubating the beads with an ezyme-bearing ligand which exhibits specific affinity for the molecular complex of particular product and ligand provided on carrier material within those beads containing a desired cell under conditions which result in affixation of enzyme-bearing ligand in those beads containing a desired cell;

(e) washing the beads free of any enzyme-bearing ligand which has not bound to molecular complexes of particular product and ligand provided on carrier material and then resuspending the beads in nutrient medium;

(f) incubating the beads in the presence of a substrate for said enzyme under conditions which cause said substrate to be converted by the enzyme into a conversion ligand exhibiting specific affinity for the ligand borne on the surface of said red blood cells within said beads;

(g) permitting sufficient time to elapse for said conversion ligand to affix within beads to the ligand on said red blood cells which exhibits affinity therefor;

(h) incubating the beads with agents comprising complement under conditions which bring about complement-mediated lysis within beads of red blood cells which carry on their surface a complex of conversion ligand and the ligand exhibiting specific affinity therefor, such lysis resulting in escape from those beads of the hemoglobin of the lysed red blood cells therein, thereby reducing the density of such beads relative to other beads;

(i) suspending said beads in a gradient medium which permits beads of distinguishable density difference to aggregate at distinguishable vertical levels in the gradient medium; and (j) separating from said gradient medium those beads which aggregate at the uppermost vertical level in said gradient medium.

* * * * *